US010832809B2

(12) United States Patent
Li et al.

(10) Patent No.: US 10,832,809 B2
(45) Date of Patent: Nov. 10, 2020

(54) CASE MANAGEMENT MODEL PROCESSING

(71) Applicant: International Business Machines Corporation, Armonk, NY (US)

(72) Inventors: Jing Li, Beijing (CN); Xiang Li, Beijing (CN); Haifeng Liu, Beijing (CN); Jing Mei, Beijing (CN); Guo Tong Xie, Beijing (CN); Yi Qin Yu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 1041 days.

(21) Appl. No.: 14/828,649

(22) Filed: Aug. 18, 2015

(65) Prior Publication Data

US 2016/0063195 A1 Mar. 3, 2016

(30) Foreign Application Priority Data

Aug. 29, 2014 (CN) .......................... 2014 1 0438036

(51) Int. Cl.
*G06Q 10/00* (2012.01)
*G06Q 50/00* (2012.01)
*G16H 40/20* (2018.01)

(52) U.S. Cl.
CPC .................. *G16H 40/20* (2018.01)

(58) Field of Classification Search
CPC .............. G16H 40/20; G06F 19/327
USPC .......................................... 705/2
See application file for complete search history.

(56) References Cited

U.S. PATENT DOCUMENTS

| 7,505,463 | B2 | 3/2009 | Schuba et al. |
| 8,126,740 | B2 | 2/2012 | Busch |
| 8,484,215 | B2 | 7/2013 | Anderson |
| 9,607,103 | B2 * | 3/2017 | Anderson ............ G06N 99/005 |

(Continued)

FOREIGN PATENT DOCUMENTS

| CN | 1707474 A | 12/2005 |
| CN | 103455015 A | 12/2013 |

(Continued)

OTHER PUBLICATIONS

Davenport et al., "Case Management and the Integration of Labor," MIT Sloan Management Review Magazine, Jan. 15, 1994, p. 1-17, Massachusetts Institute of Technology, http://sloanreview.mit.edu/article/case-management-and-the-integration-of-labor/, Accessed on Aug. 11, 2015.

(Continued)

*Primary Examiner* — Trang T Nguyen
(74) *Attorney, Agent, or Firm* — Dmitry Paskalov

(57) ABSTRACT

The present disclosure provides a method, apparatus and system for processing a case management model (CMM). According to an embodiment, there is provided a method for processing a CMM, the method includes: obtaining an existing CMM having a plurality of elements; obtaining a new CMM having at least one element; aligning an element of the new CMM to an element of the existing CMM according to match costs between the element of the new CMM and the plurality of elements of the existing CMM; and fusing the new CMM into the existing CMM based on the match cost between the aligned elements.

20 Claims, 15 Drawing Sheets

(a) COMMON SITUATION (b) EMERGENCY SITUATION (c)

(56) References Cited

U.S. PATENT DOCUMENTS

| | | | |
|---|---|---|---|
| 2002/0021838 A1* | 2/2002 | Richardson | G06F 17/2247 |
| | | | 382/181 |
| 2006/0265428 A1 | 11/2006 | Chai | |
| 2007/0011183 A1* | 1/2007 | Langseth | G06F 17/30616 |
| 2007/0150443 A1* | 6/2007 | Bergholz | G06F 17/30569 |
| 2007/0255555 A1* | 11/2007 | Crouch | G06N 5/02 |
| | | | 704/9 |
| 2009/0063470 A1* | 3/2009 | Peled | G06F 17/278 |
| 2010/0324927 A1 | 12/2010 | Tinsley | |
| 2012/0095990 A1* | 4/2012 | Lambov | G06F 17/30985 |
| | | | 707/719 |
| 2012/0166206 A1 | 6/2012 | Feely et al. | |
| 2013/0144917 A1 | 6/2013 | Hosurmath et al. | |
| 2014/0114673 A1 | 4/2014 | Hu et al. | |

FOREIGN PATENT DOCUMENTS

| | | |
|---|---|---|
| CN | 105447609 A | 3/2016 |
| WO | 2014070152 A1 | 5/2014 |

OTHER PUBLICATIONS

De Man, "Case Management: A Review of Modeling Approaches," BPTrends, Jan. 2009, p. 1-17, © Cordys.

De Man, "Case Management: Cordys Approach," BPTrends, Feb. 2009, p. 1-13, © Cordys.

Harmon, "Modeling Dynamic Processes," BPTrends Column, Nov. 5, 2013, p. 1-6.

Hinkelmann, "Case Management Model and Notation—CMMN," MSc Business Information Systems, Autumn 2013, p. 1-26.

Küster et al., "Dependent and Conflicting Change Operations of Process Models," Model Driven Architecture—Foundations and Applications, 2009, p. 158-173, LNCS vol. 5562, Springer-Verlag Berlin Heidelberg.

Le Clair et al., "Dynamic Case Management—An Old Idea Catches New Fire," Forrester for Business Process & Applications Professionals, Dec. 28, 2009, p. 1-16, Forrester Research, Inc.

Li et al., "Case Management Model Processing," English Translation Application and Drawings, Filed on Aug. 29, 2014, p. 1-61, China Patent Application Serial No. 201410438036.8.

Liu, "Case Management System," Techische Universiteit Eindhoven Master's Thesis, Nov. 2005, p. 1-64, Department of Mathematics and Computer Science, Eindhoven.

Maggi et al., "Discovering Data-Aware Declarative Process Models from Event Logs," Business Process Management, 2013, p. 1-16, LNCS vol. 8094, Springer-Verlag Berlin Heidelberg.

Marin et al., "Data Centric BPM and the Emerging Case Management Standard: A Short Survey," Business Process Management Workshops, 2013, p. 24-30, LNBIP vol. 132, Springer-Verlag Berlin Heidelberg.

Motahari-Nezhad et al., "Adaptive Case Management: Overview and Research Challenges," IEEE International Conference on Business Informatics, 2013, p. 264-269, IEEE Computer Society.

Nigam et al., "Business Artifacts: An Approach to Operational Specification," IBM Systems Journal, 2003, p. 428-445, vol. 42, No. 3, International Business Machines Corporation.

Omg, "Case Management Model and Notation," Object Management Group CMMN, May 2014, p. 1-82, Version 1.0.

Sinur, "What is the Greatest Hurdle Facing BPM?," Gartner Blogs, Apr. 29, 2009, p. 1-4, http://blogs.gartner.com/jim_sinur/2009/04/29/what-is-the-greatest-hurdle-facing-bpm/, Accessed on Aug. 11, 2015.

Swenson et al., "Mastering the Unpredictable: How Adaptive Case Management Will Revolutionize the Way That Knowledge Workers Get Things Done," 2010, 14 Pages, Meghan-Kiffer Press, Foreword and Introduction Only Provided.

Swenson et al., "Taming the Unpredictable: Real World Adaptive Case Management: Case Studies and Practical Guidance," 2011, 5 Pages, Future Strategies Inc., Foreword and Introduction Only Provided.

Van Der Aalst et al., "Case Handling: A New Paradigm for Business Process Support," Data and Knowledge Engineering, 2005, p. 1-36.

Wang et al., "X-Diff: An Effective Change Detection Algorithm for XML Documents," Proceedings of the 19th International Conference on Data Engineering (ICDE'03), 2003, p. 519-530, IEEE Computer Society.

White, "Case Management: Combining Knowledge With Process," BPTrends, Jul. 2009, p. 1-14, © Singularity.

Wikipedia, "Peter Drucker," Wikipedia: the Free Encyclopedia, Last Modified on Aug. 4, 2015, p. 1-12, https://en.wikipedia.org/wiki/Peter_Drucker, Accessed on Aug. 11, 2015.

Zhu et al., "Advanced Case Management with IBM Case Manager," IBM Redbooks, May 2013, p. 1-664, Third Edition, International Business Machines Corporation.

* cited by examiner (a) COMMON SITUATION (b) EMERGENCY SITUATION (c)

DIF TABLE

| NAME | VALUE | TIME | NEXT | ... |
|---|---|---|---|---|
| A | 0.23 | 0.1 | B | ... |
| B | N/A | 0.7 | C | ... |
| C | N/A | 0.8 | D | ... |
| D | 12.4 | 0.84 | N/A | ... |

THE TRANSFORMED CMM

TEXT MINING RESULT

4.3 Patients With Current or Prior Symptoms of HF (Stage C)
4.3.1 Patients With Reduced LVEF
Class I
9. Implantable cardioverter-defibrillator therapy is recommended for primary prevention to reduce total mortality by a education in sudden cardiac death in patients with ischemic heart disease who are at least 40 days post-MI, have an LVEF less than or equal to 80%, with NYHA functional class II or III symptoms while undergoing chronic optimal medical therapy, and have reasonable expectation of survival with a good functional status for more than 1 year (Level of Evidence: A)

- - - stage item
- - - task item
▭ data
▭ constraints

METADATA GRAPH OF TEXT MINING RESULT

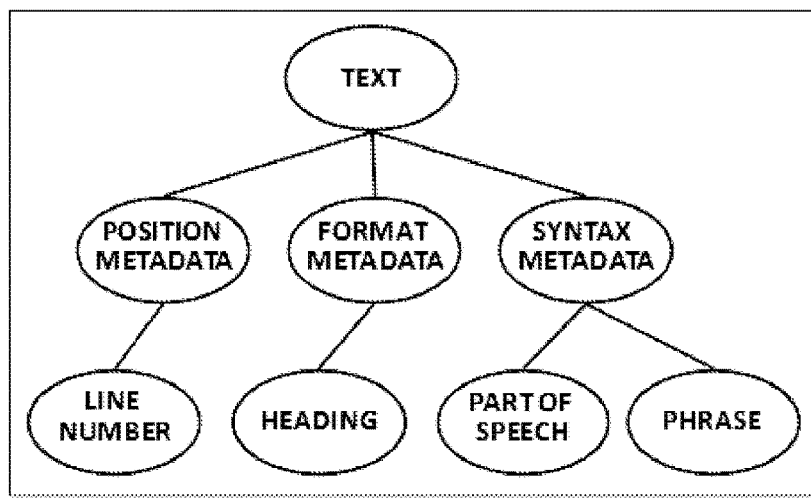

TIF TABLE

| TEXT | LINE NUMBER | HEADING | N./V. | N./V. +NUM | N./V. +ADJ. | N./V. +TMP. +N./V. | ... |
|---|---|---|---|---|---|---|---|
| ...(Stage C) | 23 | 1 | 1 | 0 | 0 | 0 | ... |
| ...LVEF | 24 | 2 | 1 | 0 | 0 | 0 | ... |
| post_MI | 27 | 0 | 1 | 1 | 1 | 0 | ... |

FIG. 5B

(a) CMM EXAMPLE IN HEALTHCARE (b) TREE DIAGRAM OF THE CMM (a) AT WITH T1 AND T2 ALIGNED

RT (b) THE FUSED RT

CASE MANAGEMENT MODEL PROCESSING

BACKGROUND

The present disclosure relates to information processing technology, and more specifically, to technology for processing a case management model.

Knowledge workers today account for a growing sector of the workforce. However, because knowledge work is less predictable than procedural process, process technologies aimed at procedural process such as business process management (BPM) cannot service knowledge workers well. Therefore, process technologies utilizing case management model (CMM) have been developed to facilitate knowledge workers' work.

Let's take the following patient-diagnosis scenario as an example, to explain the difference between BPM and CMM. In the scenario, a patient is registered at a hospital, after which he is consulted by a doctor. The doctor directs the patient to pass a blood test and a urine test. When the results of both tests become available, the doctor sets the diagnosis and defines the treatment strategy. Moreover in emergency cases, usually a registration step has to be skipped and an immediate treatment procedure has to be started. The BPMs representing the common and emergency situations are illustrated in FIGS. 1(a) and 1(b), while the CMM is illustrated in FIG. 1(c).

It can be seen that for BPM, exceptional situations have to be modeled explicitly. However, modeling of all possible scenarios results in complex models and is not feasible since exceptional situations and emergencies may arise at any point in time. This makes it difficult or even impossible to oversee what activity should be performed next.

In contrast, CMM can reduce the complexity, and allow for more flexibility in selecting an execution path. For example, when a periodical medication is prescribed to a chronic patient, only register patient and treatment tasks are executed. Thus the execution path is: register→patient treatment. In urgent visit situation, an urgent visit starts directly with consult doctor and only afterwards the task register patient is executed. It is assumed that in this case, the urine test is not necessary, while the blood test is necessary. The results of the first blood test are unclear so the treatment is executed only after the results of the second blood test become available and an additional consult doctor task. Thus the execution path is: consult doctor→register patient-→blood test→blood test→treatment. In the visit whose situation is not urgent, task register patient is performed before the task consult doctor. It is assumed that in this case, it is necessary for both urine test and blood test to be performed. However, due to alarming results of the urine test, an immediate treatment is executed to prescribe appropriate medication. The results of blood test arrive later, and an additional treatment task is executed to handle the blood test results as well. Thus the execution path becomes: register patient→consult doctor→urine test, blood test→treatment→treatment. There're even more possibilities supported by the CMM.

It can be seen that CMM represents the future trend in office automation. Therefore, it is desirable for advancement in technology to provide an improved CMM technology.

SUMMARY

According to one aspect of the present disclosure, there is provided a method for processing a case management model (CMM), the method includes: obtaining an existing CMM having a plurality of elements; obtaining a new CMM having at least one element; aligning an element of the new CMM to an element of the existing CMM according to match costs between the element of the new CMM and the plurality of elements of the existing CMM; and fusing the new CMM into the existing CMM based on the match cost between the aligned elements.

According to another aspect of the present disclosure, there is provided an apparatus for processing a case management model (CMM), the apparatus includes: aligning unit configured to receive an existing CMM having a plurality of elements and a new CMM having at least one element, align an element of the new CMM to an element of the existing CMM according to match costs between the element of the new CMM and the plurality of elements of the existing CMM; and fusing unit configured to fuse the new CMM into the existing CMM based on the match cost between the aligned elements.

BRIEF DESCRIPTION OF THE SEVERAL VIEWS OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

FIGS. 5A and 5B show examples of transformation from a structured knowledge source and an unstructured knowledge source to CMMs according to an embodiment of the present disclosure, respectively.

DETAILED DESCRIPTION

Figure 1:
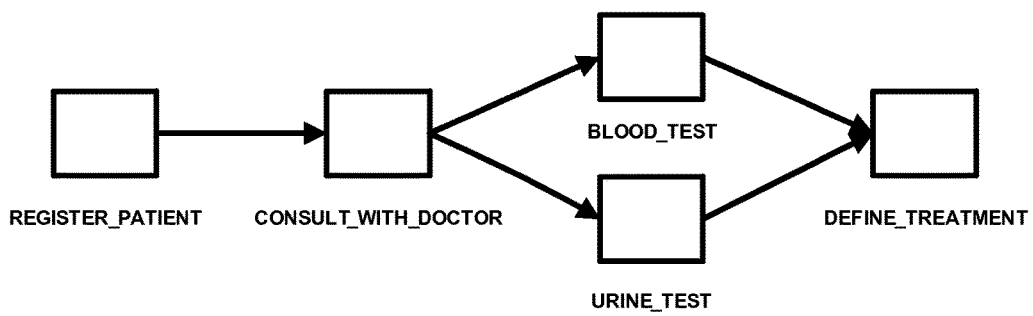
FIGS. 1(a)-1(c) show examples of BPM and CMM for healthcare scenarios.
Figure 1:
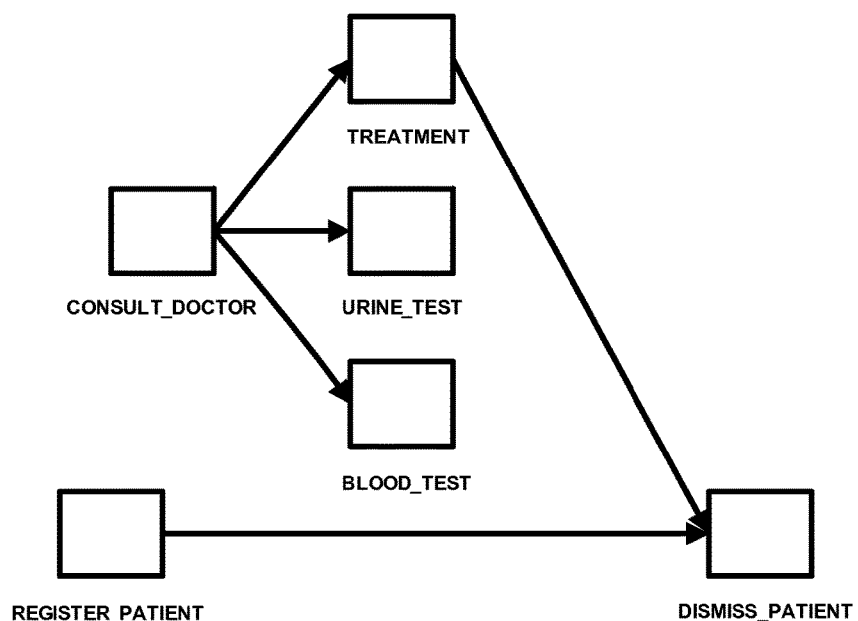
Figure 1:
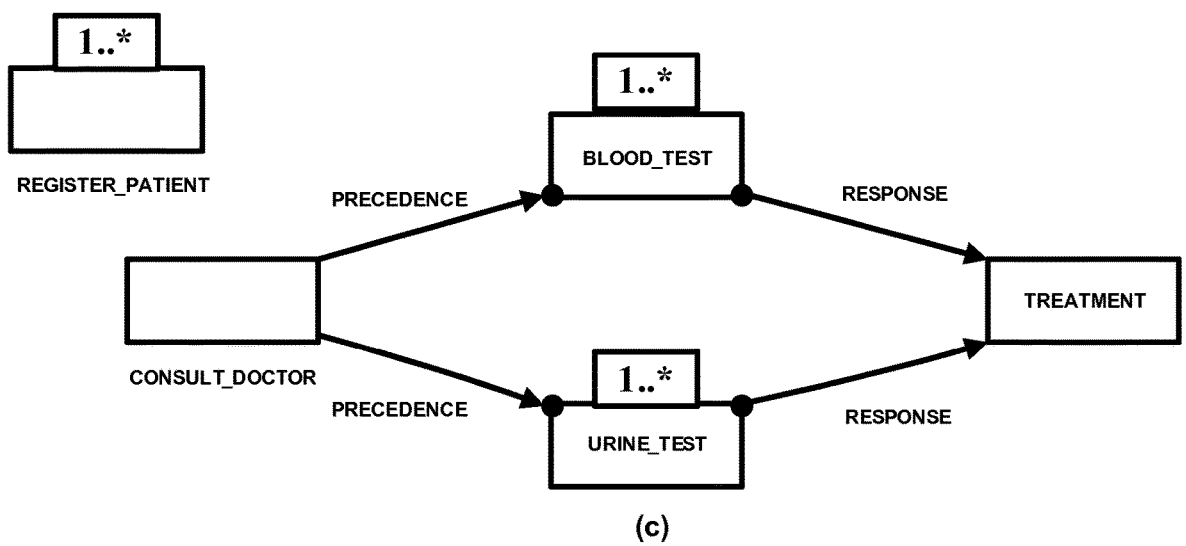

Some exemplary embodiments will be described in more detail with reference to the accompanying drawings, in which the exemplary embodiments of the present disclosure have been illustrated. However, the present disclosure can be implemented in various manners, and thus should not be construed to be limited to the embodiments disclosed herein. On the contrary, those embodiments are provided for the thorough and complete understanding of the present disclosure, and completely conveying the scope of the present disclosure to those skilled in the art.

A case refers to a process in which with respect to an object in a specific environment, a series of actions are conducted so as to achieve a desirable result. Historically, case management initially originated from law and healthcare fields. With the development of computer technology, case management model (CMM) has been applied more and more widely in more fields. Although various embodiments will be described below in the context of healthcare field, it should be noted that these embodiments can be applied in other fields as well.

As one of the industry standards, the object management group (OMG) issued "Case Management Model and Notation (CMMN) Version 1.0" in May, 2014 (OMG Document Number: formal/2014-05-05, http://www.omg.org/spec/CMMN/1.0/PDF). This standard defines meta-model for CMM, and notation for CMM modeling and model exchanging. Although various embodiments will be described below by using the notation in the above mentioned standard as an exemplary notation, it should be noted that these embodiments can be implemented based on other notations and standards as well.

A CMM usually includes entity elements and relationship elements. An entity includes stage items, task items and data. A relationship includes affiliations and constraints.

Stage serves as building block in a model, and includes, for example, the following attributes: id, name, description, entry criteria, and exit criteria. The entry criteria and exit criteria reference certain constraint(s).

A Task is an atomic unit of work, and includes, for example, the following attributes: id, name, description, inputs, outputs, entry criteria, and exit criteria. Likewise, the entry criteria and exit criteria reference certain constraint(s).

Information in data serves as context for raising events and evaluating constraint expressions as well as point of reference for item attributes, such as inputs and outputs of tasks. As input and output of a task, data includes, for example, the following attributes: id, name and value.

Affiliation constitutes hierarchy of a CMM, and includes: stage-stage affiliation representing that a stage includes other stages, and stage-task affiliation representing that a stage includes one or more tasks.

Constraint includes: item-item constraint representing temporal relationship between items, and data-item constraint representing data constraint for items.

Thus, the knowledge in a CMM include the following knowledge: item hierarchy knowledge, e.g., test stage includes blood test and urine test tasks; item temporal constraint knowledge, e.g., blood test cannot be done for a patient that has not consult doctor; data constraint knowledge, e.g., if the number of white blood cells >30000, then perform treatment.

CMM is a new paradigm for supporting flexible and knowledge intensive business processes. CMM is based on data as the typical product of these processes. That means a CMM with concise elements can represent abundant knowledge. However, the cost is that to model a case becomes more difficult for the case worker, specifically to maintain the high quality of knowledge in the model with continuous improvement, which needs to act against the following challenges: (1) out-of-date, i.e., knowledge is not reflecting current situation; (2) partial, i.e., knowledge only reflects partial situation; and (3) impractical, i.e., knowledge does not match the real situation. Existing systems can support case workers to create and edit CMMs, but it is difficult for existing systems to maintain high quality and continuously improve knowledge in the model because the existing systems face the above challenges and allow only manual improvement on CMM.

The embodiments of the present disclosure can overcome one or more of the above problems in existing systems. Hereinafter, the embodiments of the disclosure will be described with reference to FIGS. 2-13.

Figure 2A:
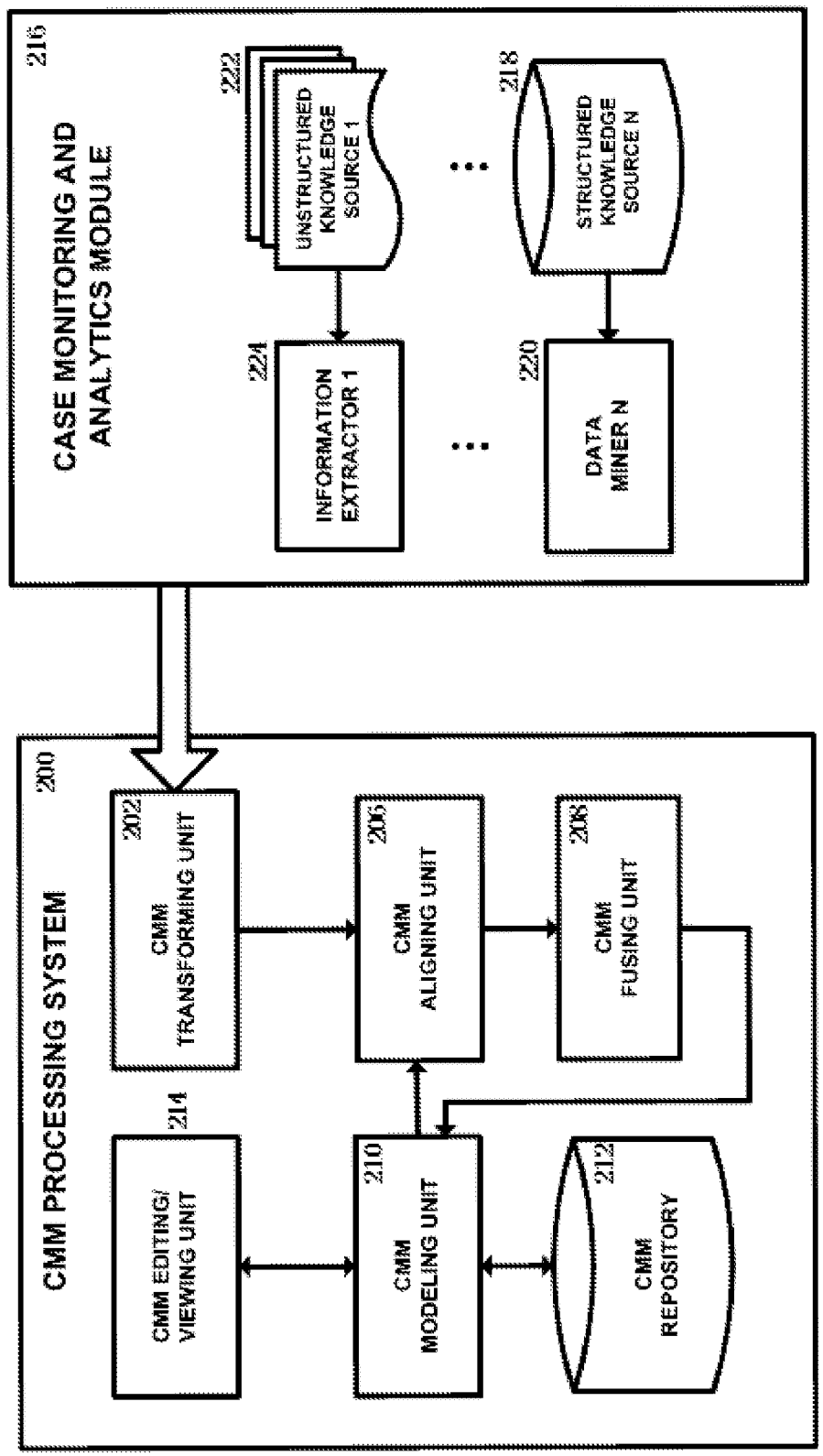
FIGS. 2A and 2B show block diagrams of CMM processing systems according to embodiments of the present disclosure, respectively.

FIG. 2A shows a block diagram of a CMM processing system according to an embodiment of the present disclosure. As shown, the CMM processing system 200 according to the embodiment of the present disclosure includes a CMM transforming unit 202, a CMM aligning unit 206, a CMM fusing unit 208, a CMM modeling unit 210, a CMM repository 212 and a CMM editing/viewing unit 214.

The CMM transforming unit 202 is configured to receive information extracted from various knowledge sources including structured knowledge source and unstructured knowledge source and transform it to a CMM. For example, the information extracted from various knowledge sources is provided by a case monitoring and analytics module 216. The CMM transforming unit 202 is implemented by performing the CMM transforming process described below with reference to FIG. 4.

With respect to the above case monitoring and analytics module 216 which communicates with the CMM transforming unit 202, it is configured to extract information from various knowledge sources including structured knowledge source and unstructured knowledge source. As shown, the case monitoring and analytics module 216 includes at least one structured knowledge source 218 and at least one unstructured knowledge source 222, as well as at least one data miner 220 and at least one information extractor 224 corresponding to the knowledge sources 218 and 222 respectively.

The structured data provided by the structured knowledge source 218 generally refers to data which has fixed structure and can be interpreted directly by a machine, and includes data managed by a database and other data expressed in two or more dimensional structures, e.g., records about production, business, transaction, customer information, etc. In comparison with the structured data, the unstructured data provided by the unstructured knowledge source 222 mainly refers to data which can be understood by a person but cannot be interpreted directly by a machine, and includes various contents that cannot be expressed by digit value or uniform structure, e.g. operation content such as contract, invoice, letter, and purchase record, department content such as document, brief report, archives and email, web page content, multimedia content such as audio, movie and image, etc. The structured knowledge source 218 and the unstructured knowledge source 222 is provided by various entities depending upon the specific application scenario. For example, in the scenario related to healthcare, the structured knowledge source 218 includes patient database, prescription database, etc., and the unstructured knowledge source 222 includes medical guide, treatment procedure, academic papers, etc.

The data miner 220 is configured to mine data from structured knowledge sources. For example, the data miner 220 utilizes existing and future developed information techniques such as statistical method, artificial intelligence method, machine learning method, neural network technique, etc., to extract from a structured database, implicitly existing knowledge, relationship and other meaningful patterns, etc. In an exemplary example, the data miner 220 is implemented for example by using Intelligent Miner for Data (IBM Inc.), Enterprise Miner (SAS Inc.), Insightful Miner (Insightful Inc.), etc.

The information extractor 224 is configured to extract information from unstructured knowledge sources. For example, the information extractor 224 extracts information from unstructured knowledge sources such as text, by performing named entity recognition, coreference resolution, relationship extraction and language and vocabulary analysis, etc. In an exemplary example, the information extractor 224 extracts from text which is an important constituent of unstructured knowledge source, various metadata about text including position metadata (e.g., line number), format metadata (e.g., heading) and syntax metadata (e.g., part of speech and phrase), as shown in FIG. 5B. The position metadata and the format metadata is obtained directly from text (e.g., headings have highlighted styles). The syntax metadata is extracted through existing and future developed syntactic parsing technique, machine learning technique using corpus, etc. For example, the information extractor 224 is implemented by using Intelligent Miner for Text (IBM Inc.), Text Miner (SAS Inc.), etc.

Continued from the CMM transforming unit 202, the components of the CMM processing system will be described. The CMM aligning unit 206 is configured to receive a CMM transformed by the CMM transforming unit 202 and an existing CMM modeled by the CMM modeling unit 210, and align the received CMM to a matching location in the existing CMM. The CMM fusing unit 208 is configured to fuse the received CMM into the existing CMM according to the aligning result provided by the CMM aligning unit 206. The CMM fusing unit 208 further provides the fused CMM to the CMM modeling unit 210. For example, the CMM aligning unit 206 is implemented by performing the aligning process and the aligning subprocess described below with reference to FIGS. 6 and 7. The CMM fusing unit 208 is implemented by performing the compounding process and the inserting process described below with reference to FIGS. 10 and 11.

The CMM modeling unit 210 enables a user to build a CMM. The CMM modeling unit 210 further provides the built CMM to the CMM aligning unit 206, and further receives the fused CMM from the CMM fusing unit. For example, the CMM modeling unit 210 is implemented by using existing product, IBM Case Manager.

The CMM repository 212 stores the CMM modeled by the CMM modeling unit 210, and provide the stored CMM to the CMM modeling unit when needed by the CMM modeling unit. For example, the CMM repository 212 is implemented by using various existing and future developed storage systems.

The CMM editing/viewing unit 214 enables a user to edit/view (e.g., through a user interface) the CMM modeled by the CMM modeling unit 210, and to edit/view the fused CMM received by the CMM modeling unit 210. For example, the CMM editing/viewing unit 214 is also implemented by using existing product, IBM Case Manager.

Figure 2B:
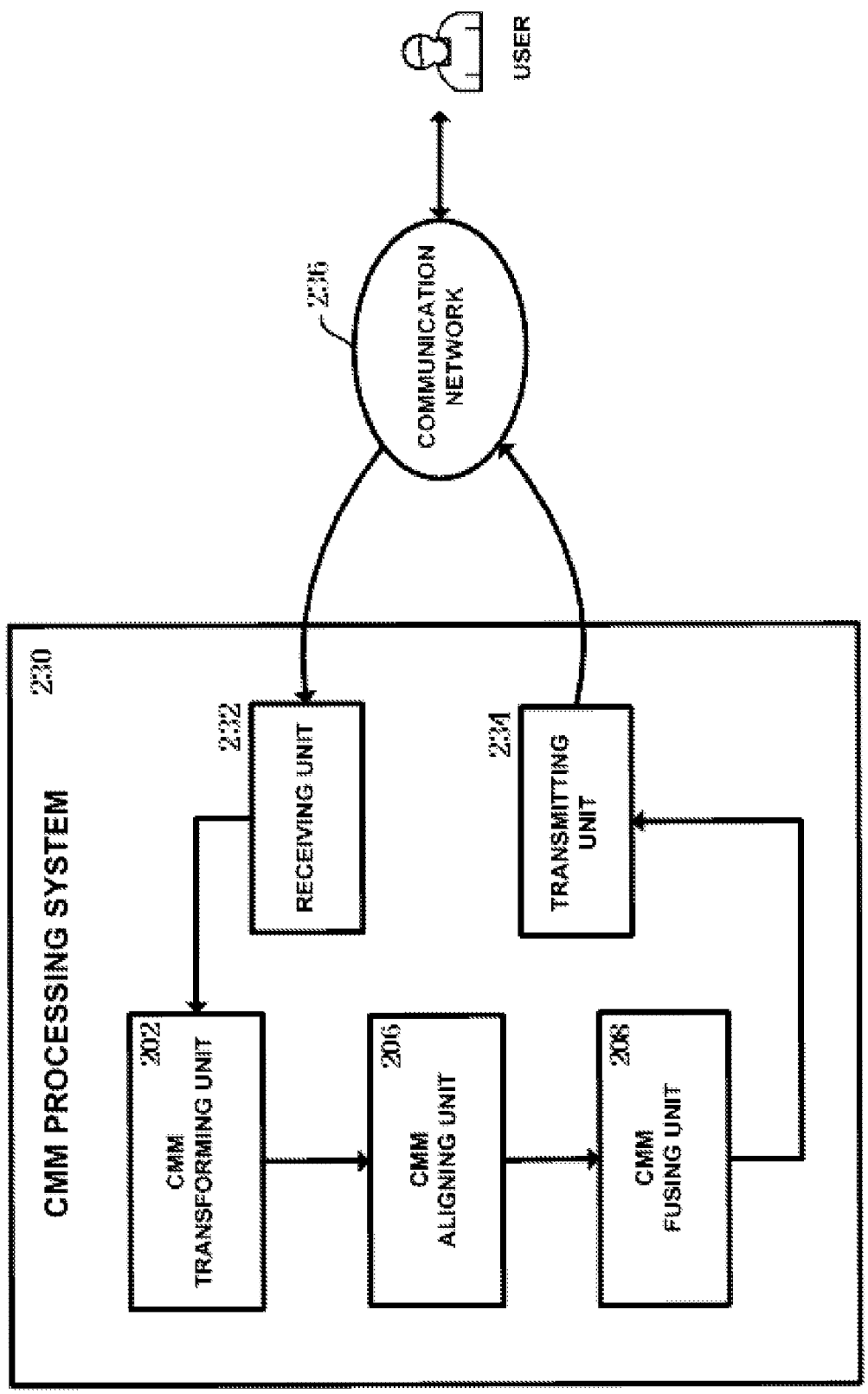

FIG. 2B shows a block diagram of a CMM processing system 230 according to another embodiment of the present disclosure. As shown, the CMM processing system 230 according to the embodiment of the present disclosure includes a receiving unit 232, a CMM transforming unit 202, a CMM aligning unit 206, a CMM fusing unit 208 and a transmitting unit 234.

The receiving unit 232 is configured to receive an existing CMM and information extracted from various knowledge sources through a communication network 236 (including wired communication network and wireless communication network) from a user who needs CMM fusing service.

The CMM transforming unit 202 is configured to transform to a new CMM the information which is extracted from various knowledge sources and received by the receiving unit. The CMM aligning unit 206 is configured to align the new CMM transformed by the CMM transforming unit 202 to a matching location in the existing CMM received by the receiving unit 232. The CMM fusing unit 208 is configured to fuse the new CMM (transformed by the CMM transforming unit 202) into the existing CMM (received by the receiving unit 232), according to the aligning result provided by the CMM aligning unit 206. For example, the CMM transforming unit 202, the CMM aligning unit 206 and the CMM fusing unit 208 is implemented by using the same implementing manners as those of the corresponding units shown in FIG. 2A, and thus their related description is omitted here.

The transmitting unit 234 is configured to transmit the CMM fused by the CMM fusing unit 208 through the communication network 236 to the user who needs CMM fusing service. For example, the receiving unit 232 and the transmitting unit 234 is implemented by using any components (e.g., network adapter, modem, etc.) which enable a computer to communicate with a network.

It should be noted that although the CMM aligning unit 206 and the CMM fusing unit 208 are depicted as separate components in the CMM processing systems 200 and 230 in FIGS. 2A and 2B, in another embodiment, the CMM aligning unit 206 and the CMM fusing unit 208 is combined as one apparatus, or the CMM aligning unit 206 and the CMM fusing unit 208 is combined with the CMM transforming unit 202 to become one apparatus.

It should be also noted that the above mentioned "CMM" includes a CMM built by a user through the CMM modeling unit 210, and a CMM transformed by the CMM transforming unit 202. As to the transformed CMM, it is in nature a set being containing CMM elements and relationships therebetween which are obtained by transforming the information extracted from knowledge sources. Because the set comes from knowledge sources, the size of the set varies according to the size of knowledge sources. When the size of knowledge sources is small (e.g., one or several paragraphs of text), the set only contains a small amount of CMM elements and relationships therebetween. At this time, the set is regarded as CMM pieces. For example, if the case monitoring and analytics module 216 sends the information extracted from various knowledge sources to the CMM transforming unit 202 in real time or every time when a relatively short time period has elapsed, or if the amount of the extracted information which is transmitted to the CMM transforming unit 202 by the user who needs CMM fusing service is small, the above set transformed by the CMM transforming unit 202 is regarded as CMM pieces. On the other hand, when the size of knowledge sources is large (e.g., an article detailing various aspects of the operational procedure), the above set contains large amount of CMM elements and relationships therebetween. At this time, the set is regarded as a new CMM. For example, if the case monitoring and analytics module 216 sends the information extracted from various knowledge sources to the CMM transforming unit 202 every time when a relatively long time period has elapsed, or if the amount of the extracted information which is transmitted to the CMM transforming unit 202 by the user who needs CMM fusing service is large, the above set transformed by the CMM transforming unit 202 is regarded as a new CMM. Therefore, the CMM transformed by the CMM transforming unit 202 can cover CMM pieces.

Figure 3:
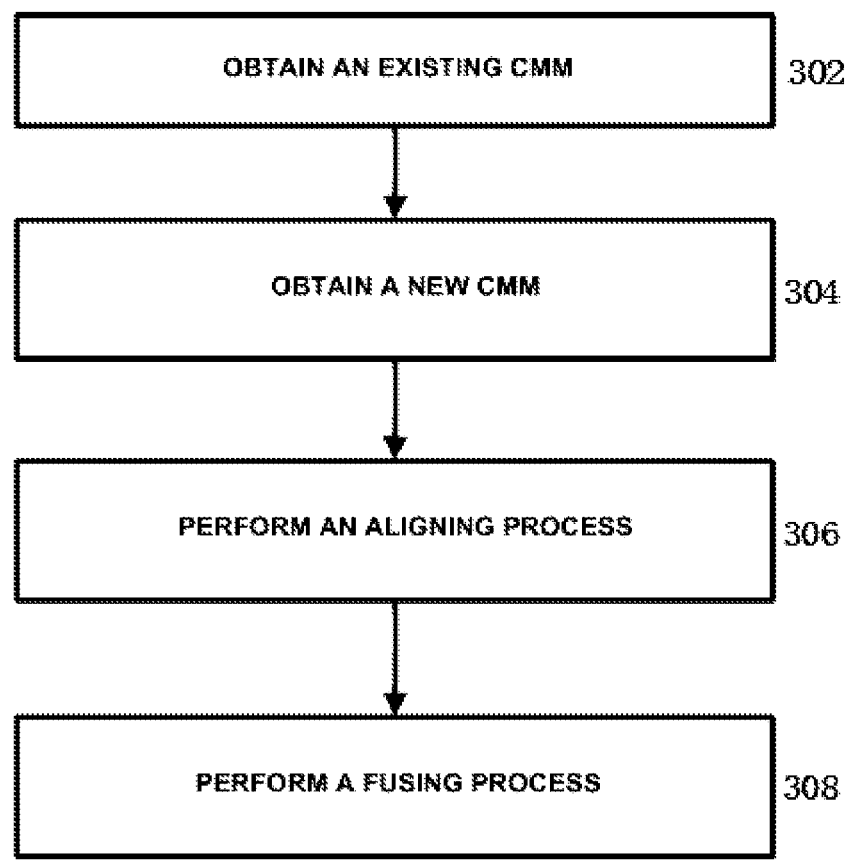
FIG. 3 shows a flow chart of a CMM processing method according to an embodiment of the present disclosure.
Figure 6:
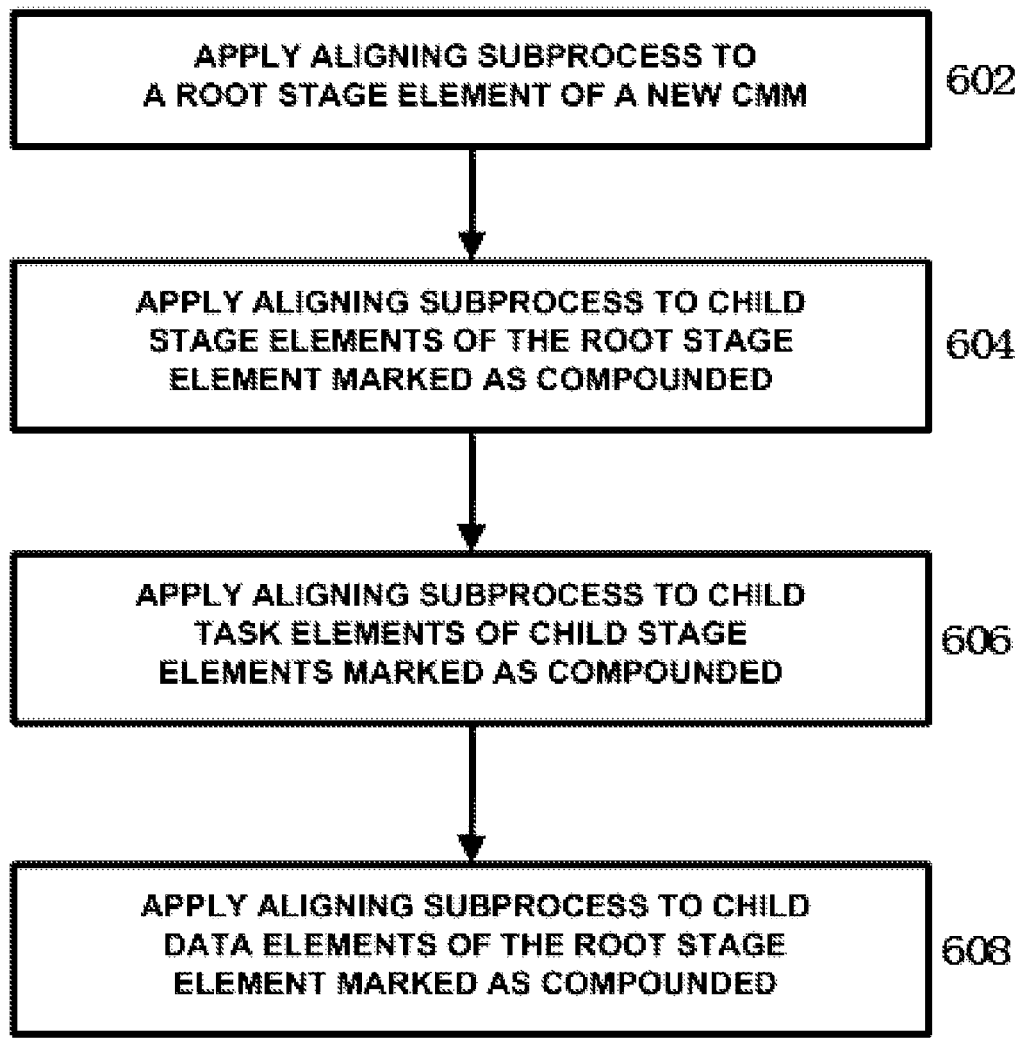
FIG. 6 shows a flow chart of an aligning process according to an embodiment of the present disclosure.
Figure 10:
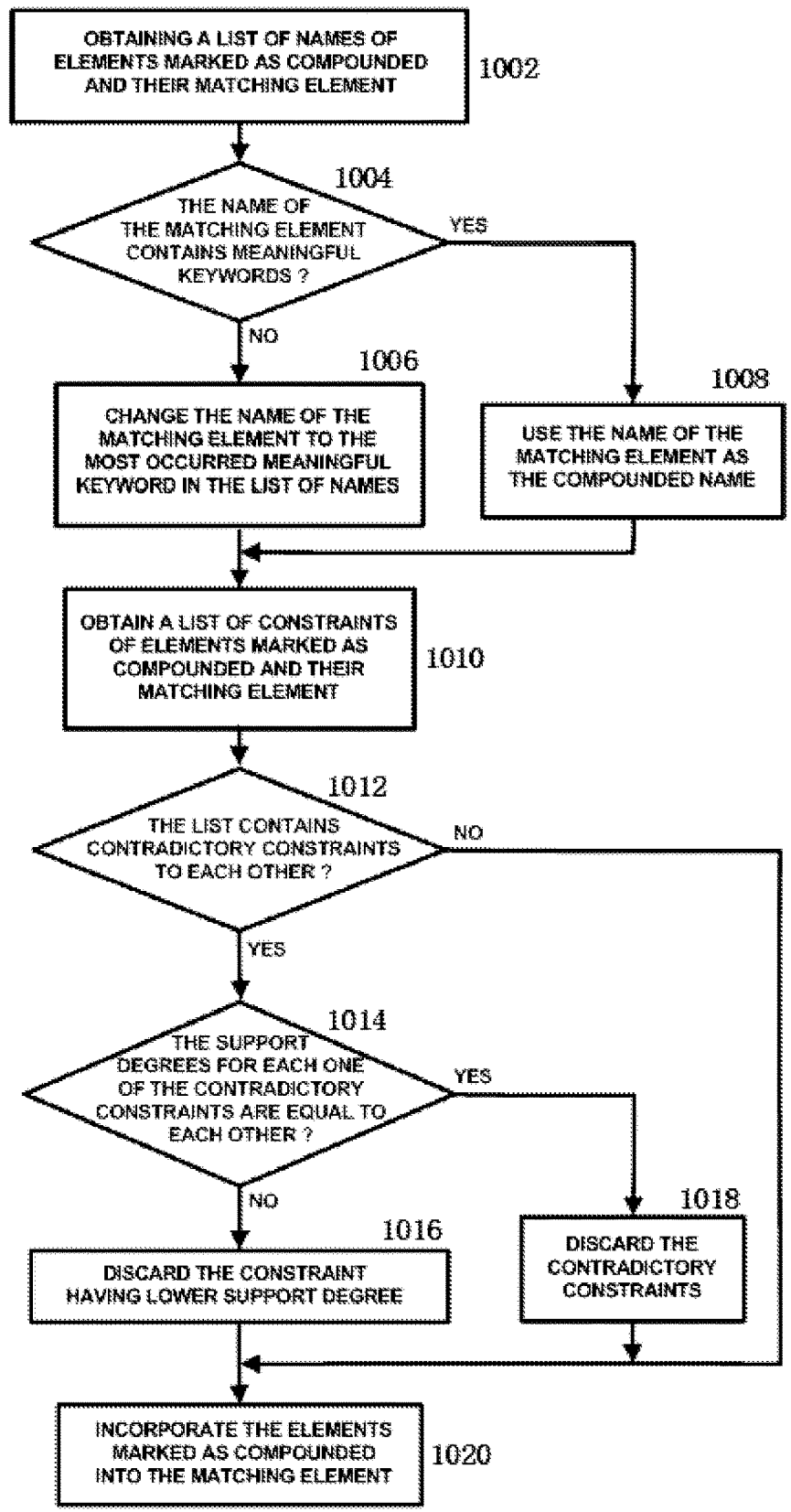
FIG. 10 shows a flow chart of a compounding process according to an embodiment of the present disclosure.
Figure 11:
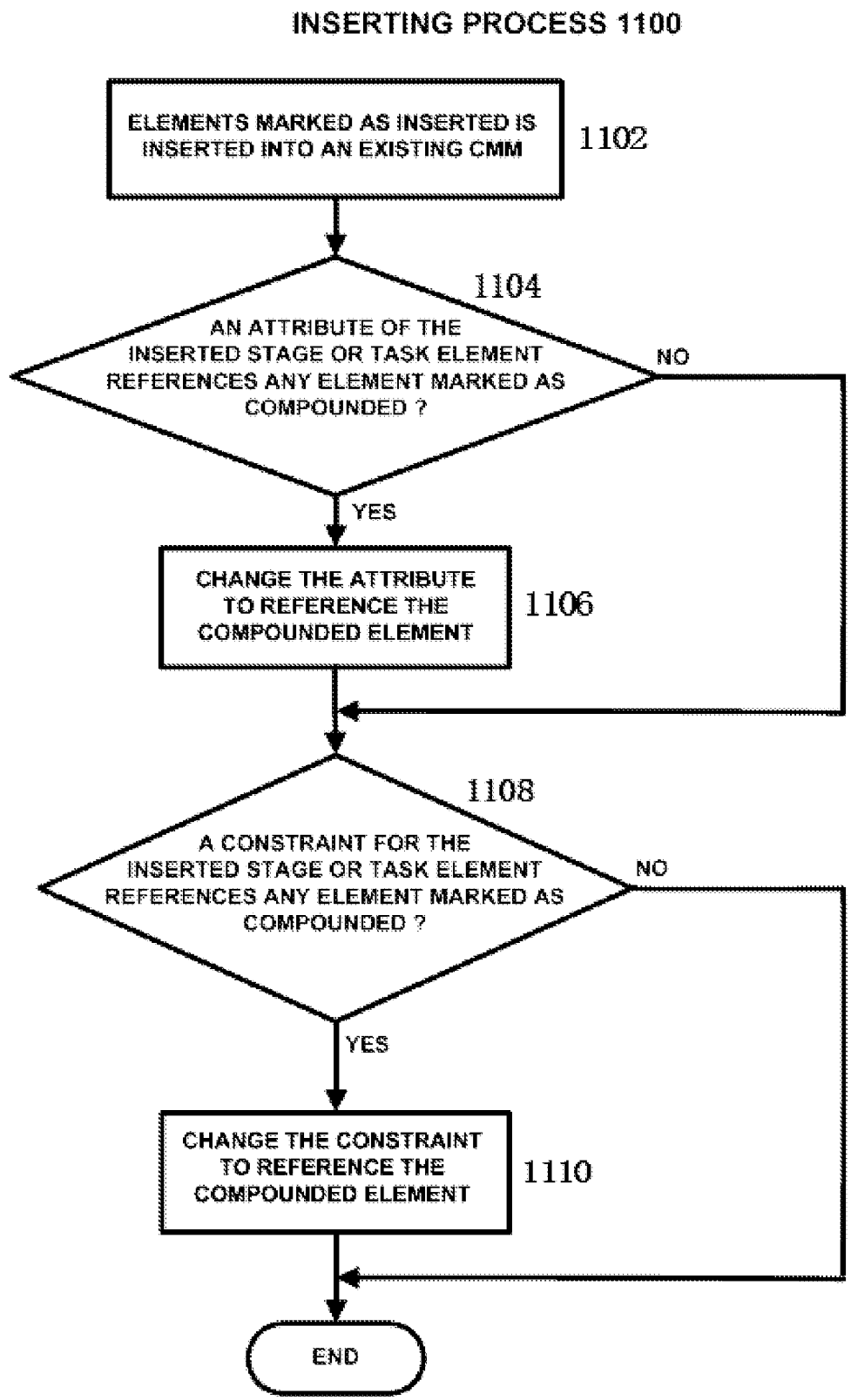
FIG. 11 shows a flow chart of an inserting process according to an embodiment of the present disclosure.

FIG. 3 shows a flow chart of a CMM processing method according to an embodiment of the present disclosure. In step 302, an existing CMM is obtained. As described above with respect to FIGS. 2A and 2B, the existing CMM is built by a user by using the CMM modeling unit 210, and is also received through a communication network from a user who needs CMM fusing service. Then, in step 304, a new CMM is obtained. As described above with respect to FIGS. 2A and 2B, the new CMM is transformed by the CMM transforming unit 202. Then, in step 306, an aligning process which is described later with reference to FIG. 6 is performed. Then, in step 308, a compounding process and an inserting process which are described later with reference to FIGS. 10 and 11 is performed. The compounding process and the inserting process is collectively referred to as fusing process. It should be noted that although the steps 302 and 304 are depicted to be performed sequentially in FIG. 3, the steps 302 and 304 can of course be performed in parallel or in a reverse order.

Figure 4:
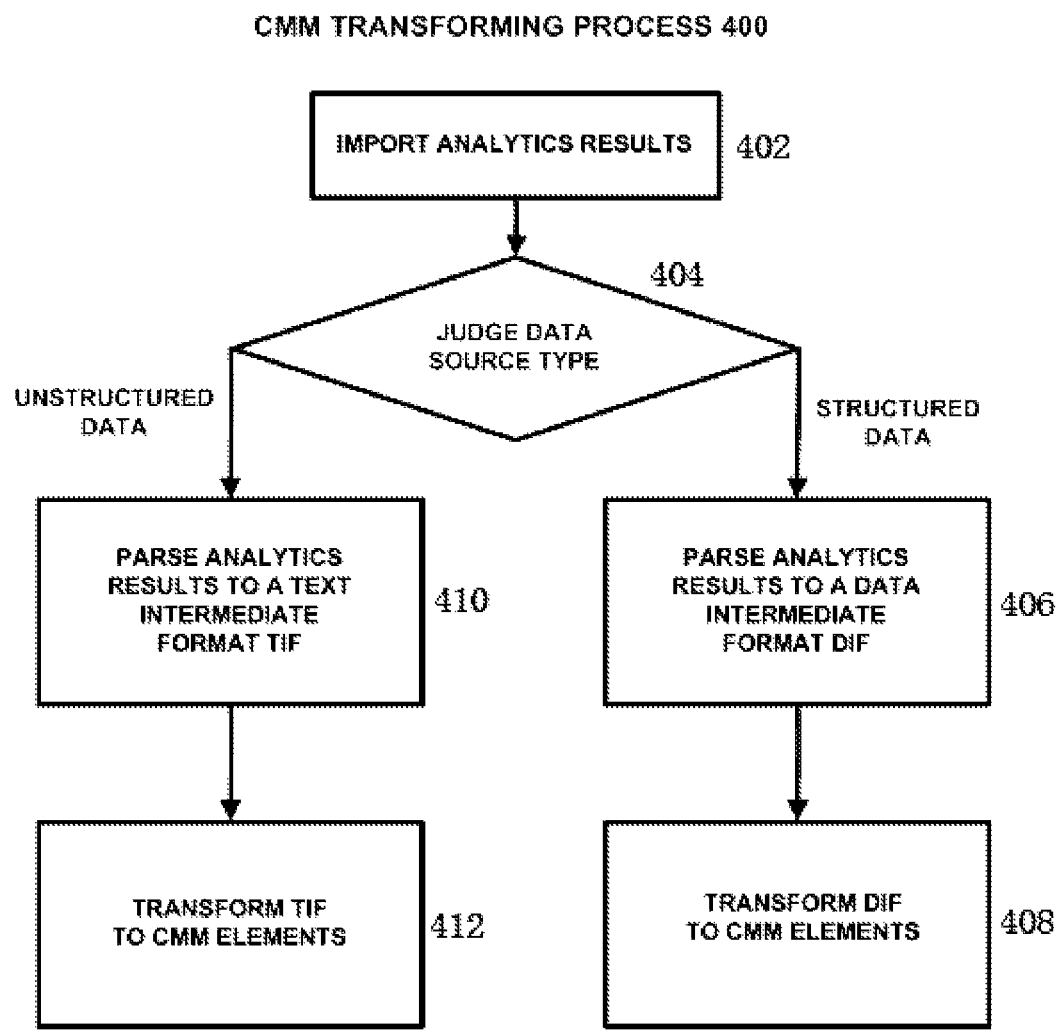
FIG. 4 shows a flow chart of a CMM transforming process according to an embodiment of the present disclosure.

FIG. 4 shows a CMM transforming process according to an embodiment of the present disclosure. As shown in FIG. 4, firstly, in step 402, analytics results are imported. As described above, for example, the analytics results are received from the case monitoring and analytics module 216, or be received through a communication network from a user who needs CMM fusing service.

Figure 5A:
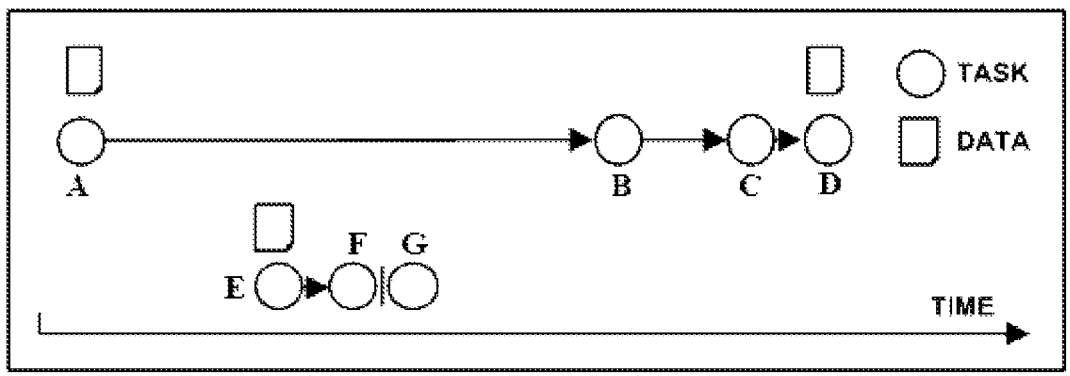
Figure 5A:
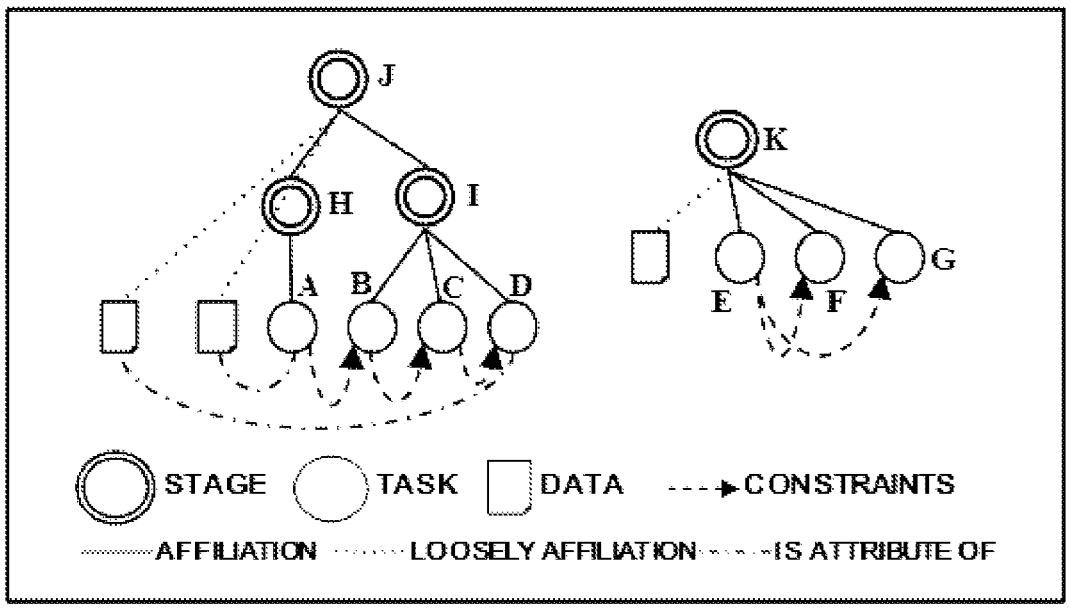

Then, in step 404, the type of the data source is judged. For example, the type of the data source is judged by means of an identifier sent along with the analytics results. If it is judged in step 404 that the data source is structured data, the analytics results are parsed to a data intermediate format (DIF) in step 406. FIG. 5A shows an example of mined results and a DIF table for structured data. As shown in the upper portion of FIG. 5A, the temporal relationships between four events has been mined from a database by using for example statistical method. As shown in the middle portion of FIG. 5A, for example, an empty DIF table is built up at first. Each line of the DIF table contains one mined event, and each column of the DIF table corresponds to the name, value, time, next event, etc. Then, for each mined event, the value for each column is obtained and filled into the DIF table.

Then, in step 408, the DIF table is transformed to CMM elements. For example, firstly, the event is mapped to task, the value is mapped to data, and the next event is mapped to constraint. Then, the events are clustered by time, and each cluster is mapped to stage. For example, in the example shown in FIG. 5A, as to the first data mining result in the upper portion of FIG. 5A, the tasks B, C, and D are clustered by time to form stage I. Thus, the task A is affiliated to stage H, and the stages H and I are affiliated to root stage J. As to the second data mining result in the upper portion of FIG. 5A, the tasks E, F and G are closely located on time axis, as exemplarily shown in the upper portion of FIG. 5A, and after the task E, the task is F or G. Thus, the tasks E, F, and G are clustered by time to form stage K.

On the other hand, if it is judged in step 404 that the data source is unstructured data such as text, the analytics results are parsed to a text intermediate format (TIF) in step 410. FIG. 5B shows an example of mined results and a TIF table for unstructured data. The upper portion of FIG. 5B shows the result obtained by conducting text mining on one portion of the medical guide about chronic heart failure (CHF). For ease of understanding, the text of this portion of the medical guide is provided as follows:

4.3. Patients with Current or Prior Symptoms of HF (Stage C)
4.3.1. Patients with Reduced LVEF
Class I
9. Implantable cardioverter-defibrillator therapy is recommended for primary prevention to reduce total mortality by an education in sudden cardiac death in patients with ischemic heart disease who are at least 40 days post-MI have an LVEF less than or equal to 30%, with NYHA functional class II or III symptoms while undergoing chronic optimal medical therapy, and have reasonable expectation of survival with a good functional status for more than 1 year (Level of Evidence: A).

The middle portion of FIG. 5B shows metadata graph of the text mining result. Text includes position metadata, format metadata and syntax metadata. In this example, the position metadata is in the form of line number, the format metadata is in the form of heading, and the syntax metadata is in the form of part of speech and phrase. As shown in the lower portion of FIG. 5B, for example, an empty TIF table is built up at first. Each line of the TIF table contains one analytics record, and each column of the TIF table corresponds to one leaf node of the text metadata graph (i.e., line number, heading, part of speech and phrase, etc.). Then, for each analytics record, the value for corresponding metadata is obtained, and the analytics record and all values for metadata are filled into the TIF table.

Then, in step 412, the TIF table is transformed to CMM elements. For example, heading is mapped to stage, noun/verb associated with a value is mapped to data, noun/verb is mapped to task, noun/verb+temporal relationship+noun/verb is mapped to constraint, affiliation between headings and between content and headings are mapped to affiliation, adverb and adjective words associated with stage, task and data is mapped to constraint, the value of data is mapped to data constraint, and so on. Specifically, in the example shown in the upper portion of FIG. 5B, the mapping result is as follows:

Line 23: "Patients With Current or Prior Symptoms of HF (Stage C)" belongs to headings, and thus is mapped to stage;

Line 24: "Patients With Reduced LVEF" belongs to headings, and thus is mapped to stage;

Line 25: "Class I" belongs to headings, and thus is mapped to stage;

Line 26: "Implantable cardioverter-defibrillator therapy" belongs to noun/verb, and thus is mapped to task;

Line 27: "at least 40 days" belongs to the value of data, and thus is mapped to data constraint;

"post-MI" belongs to noun/verb associated with a value, and thus is mapped to data;

"LVEF" belongs to noun/verb associated with a value, and thus is mapped to data; "less than or equal to 30%" belongs to the value of data, and thus is mapped to data constraint;

Line 28: "NYHA functional class" belongs to noun/verb associated with a value, and thus is mapped to data;

"II or III" belongs to the value of data, and thus is mapped to data constraint;

Line 29: "survival with a good functional status" belongs to noun/verb associated with a value, and thus is mapped to data;

"more than 1 year" belongs to the value of data, and thus is mapped to data constraint.

For example, the transformation from the TIF table to CMM elements are implemented using the following program flow:
1. input TIF data, empty list of case model piece L
2. sort TIF records by line
3. for each record r in TIF table
    1. if r.heading>0, s=new Stage{r.text, ..}; sp=getParent( ); /*if the heading value of r>0, assign r to stage s, and look for the parent sp for s */
        1. if sp==null, L.add(s); /*if sp is null, add s into L */
        2. else, sp.addChild(s); /*otherwise, add s as a child of sp */
    2. else if r.heading==0, /*if the heading value of r=0 */
        1. if r.nv==1 & r.num==1, d=new Data{r.text, r.value}; dt=getTask( ); dt.addOutput(d) /*if the value for noun/verb=1 and the value for number=1, assign r to data d, obtain the task dt that d belongs to, add d as output of dt */
        2. if r.nv==1 & r.num==0, t=new Task{..}; /*if the value for noun/verb=1 and the value for number=0, assign r to task t */
        tp=getParent( ) /*get the parent tp for t */
            1. if tp==null, L.add(t); /*if tp is null, add t */
            2. else, tp.addChild(t); /*otherwise, add t as a child of tp */
        3. If r.nvtmpnv==1, t.add(new Constraint(tmp)); /*if the value for noun/verb+temporal relationship+ noun/verb=1, add temporal relationship as constraint for t*/
4. output L It should be noted that the manner in which the mining is performed on various components of text and the specific components are mapped to corresponding CMM elements in the above embodiment is only an exemplary manner, the mined components and the mapping manner are adjusted according to the specific application scenario for the CMM.

Figure 7:
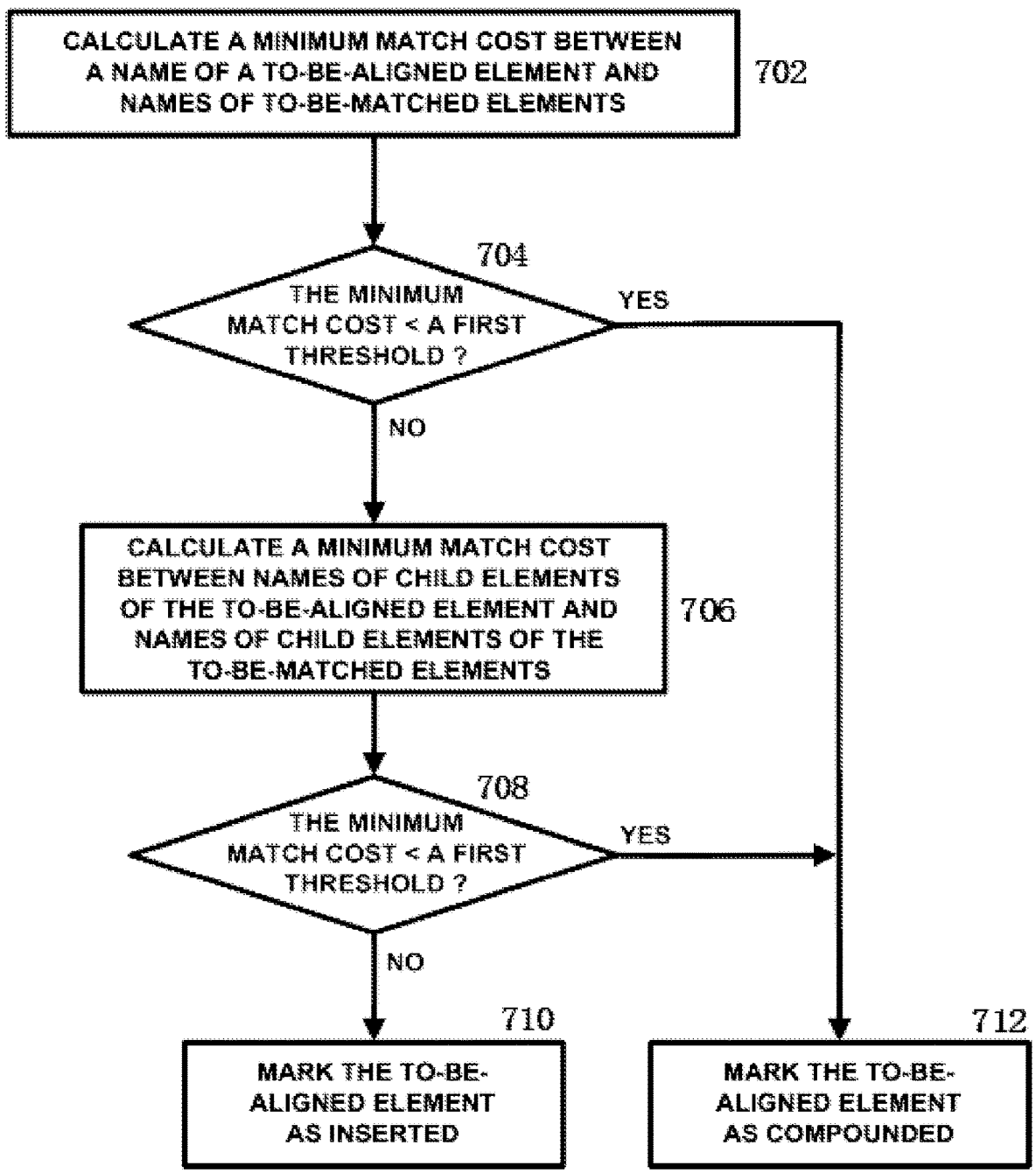
FIG. 7 shows a flow chart of an aligning subprocess according to an embodiment of the present disclosure.

FIG. 6 shows a flow chart of an aligning process according to an embodiment of the present disclosure. As shown in FIG. 6, firstly, in step 602, the aligning subprocess which is described later with reference to FIG. 7 is applied to a root stage element of a new CMM. As described earlier, the new CMM may be transformed by the CMM transforming unit 202, an existing CMM is provided by the CMM modeling unit 210. For example, the aligning subprocess is applied to the root stage element of the new CMM and respective stage elements of the existing CMM. As described later with reference to FIG. 7, the result obtained by performing the aligning subprocess is that the root stage element is either marked as compounded with one stage element of the existing CMM, or marked as inserted into the existing CMM. Generally, the existing CMM has been built to be relatively complete, and thus the root stage element of the new CMM is marked as compounded with one stage element of the existing CMM. However, there also exists possibility that the existing CMM is not quite complete. In this case, the root stage element is marked as inserted. That is, the root stage element is inserted into the existing CMM as a root stage element of the existing CMM.

As to the root stage element marked as inserted, there is no need to apply further aligning operation to its child elements. Thus, in step 604, the aligning subprocess is applied to the child stage elements of the root stage element which is marked as compounded. For example, the aligning subprocess is applied to the child stage elements of the root stage element in the new CMM marked as compounded, and the child stage elements of the matching stage element (i.e., one stage element in the existing CMM which is marked as compounded with the root stage element of the new CMM). Likewise, the result obtained by performing the aligning subprocess is that the child stage elements of the root stage element which is marked as compounded is either marked as compounded with one child stage element of the matching stage element of the existing CMM, or marked as inserted into the existing CMM as a child stage element.

Likewise, as to a child stage element marked as inserted, there is no need to apply further aligning operation to its child elements. Thus, in step 606, the aligning subprocess is applied to the child task elements of a child stage element which is marked as compounded. For example, the aligning subprocess is applied to the child task elements of the child stage element in the new CMM marked as compounded, and the child task elements of the matching stage element (i.e., one stage element in the existing CMM which is marked as compounded with the child stage element of the new CMM). Likewise, the result obtained by performing the aligning subprocess is that the child task elements of the child stage element which is marked as compounded is either marked as compounded with one child task element of the matching stage element in the existing CMM, or marked as inserted into the existing CMM as a child task element.

As to data elements, because they are placed as leaf nodes of a root stage element, in step 608, the aligning subprocess is applied to the child data elements of the root stage element which is marked as compounded. For example, the aligning subprocess is applied to the child data elements of the root stage element in the new CMM marked as compounded, and the child data elements of the matching stage element (i.e., one stage element in the existing CMM which is marked as compounded with the root stage element of the new CMM). Likewise, the result obtained by performing the aligning subprocess is that the child data elements of the root stage element which is marked as compounded is either marked as compounded with one child data element of the matching stage element of the existing CMM, or marked as inserted into the existing CMM as a child data element. It should be noted that although step 608 is depicted to be sequentially performed after step 606 in FIG. 6, step 608 is also be performed before step 604 or in parallel with step 604.

In this way, by performing the above aligning process, all stage, task and data elements in the new CMM is either marked as compounded, or marked as inserted. In one embodiment, when the stage, task and data elements in the new CMM are marked as compounded or inserted, their attributes are marked as compounded or inserted correspondingly, and the constraints for the stage and task elements are marked as compounded or inserted correspondingly.

It should be noted that in a case where a plurality of new CMMs are fused into an existing CMM, in the above aligning process, when aligning the second new CMM after the first new CMM has been aligned to the existing CMM, the to-be-matched existing CMM contains the first new CMM which has been previously aligned. Likewise, when aligning the third new CMM, the to-be-matched existing CMM contains the first and second new CMMs which have been previously aligned. The same holds true for aligning the fourth new CMM, the fifth new CMM, and so on.

FIG. 7 shows a flow chart of an aligning subprocess according to an embodiment of the present disclosure. As shown in FIG. 7, firstly, in step 702, a minimum cost between a name of a to-be-aligned element and names of to-be-matched elements are calculated. The to-be-aligned element and the to-be-matched elements have been described above with reference to FIG. 6. In the present embodiment, for example, match cost is calculated by using edit distance. Edit distance is also referred to as Levenshtein distance, and refers to the minimum number of edit operations required to transform one string into the other string. The allowed edit operations include substitution of one character for another, insertion or removal of a single character. The edit distance is calculated by using various kinds of algorithms including dynamic programming algorithm. As an exemplary example, let X be the name of the to-be-aligned element, and let Y be the names of the to-be-matched elements, the minimum match cost is calculated by using the formula: Mmin1(X,Y)=Min(Dist(X,Y)/[StringLength(X+Y)]), wherein Dist represents edit distance, StringLength represents length of a string. It should be noted that calculating the match cost using edit distance is only an exemplary example, the match cost is also calculated by using other metrics characterizing the similarity between two strings. It should also be noted that because the number of the to-be-matched elements is generally more than one, the expression Min(Dist(X,Y)/[StringLength(X+Y)]) in the above formula for calculating the minimum match cost actually represents the set: {Dist(X,Y1)/[StringLength(X+Y$_1$)], . . . , Dist(X,Y$_n$)/[StringLength(X+Y$_n$)]}.

Then, in step 704, it is judged whether the minimum match cost is smaller than a first threshold. If it is judged that the minimum match cost is smaller than the first threshold, the to-be-aligned element is marked as compounded with the matching element (i.e., one element in the existing CMM which has the minimum match cost with the to-be-aligned element) in step 712.

On the other hand, if it is judged in step 704 that the minimum match cost is larger than or equal to the first threshold, a minimum match cost between names of child elements of the to-be-aligned element and names of child elements of the to-be-matched elements are calculated in step 706. When the to-be-aligned element is stage, its child elements are stage, task and data. In one exemplary example, let x be the name of a child element of X, and let X$_{chd}$ and Y$_{chd}$ be sets of names of child elements of X and Y respectively, the minimum match cost is calculated by using the formula:

$$M_{min2}(X,Y) = \mathrm{Min}[\Sigma_{x \ in \ X_{chd}} M_{min1}(x, Ychd)/(\text{number of } x \text{ in } X_{chd})].$$

Likewise, because the number of the to-be-matched elements is generally more than one, the expression $\Sigma_{x \ in \ Xchd} M_{min1}(x, Ychd)/(\text{number of } x \text{ in } X_{chd})$ in the above formula for calculating the minimum match cost actually represents the set:

$$\{\Sigma_{x \ in \ Xchd} M_{min1}(x, Y^1_{chd})/(\text{number of } x \text{ in } X_{chd}), \ldots,$$

$$\Sigma_{x \ in \ Xchd} M_{min1}(x, Y^n_{chd})/(\text{number of } x \text{ in } X_{chd})\}.$$

It should be noted that X$_{chd}$ and Y$_{chd}$ are the name of X and the name of Y, respectively.

It should be noted that because task element and data element does not contain any child element, the processing of steps 706 and 708 are skipped when the to-be-aligned element is task element or data element.

Then, in step 708, it is judged again whether the newly calculated minimum match cost is smaller than the first threshold. If it is judged in step 708 that the newly calculated minimum match cost is smaller than the first threshold, the to-be-aligned element is marked as compounded with the matching element (i.e., one element in the existing CMM which has the minimum match cost with the to-be-aligned element) in step 712.

On the other hand, if it is judged in step 708 that the newly calculated minimum match cost is larger than or equal to the first threshold, the to-be-aligned element is marked as inserted into the existing CMM. As described earlier, generally, the existing CMM has been built to be relatively complete, and thus the root stage element of the new CMM is marked as compounded with one stage element of the existing CMM. However, there also exists possibility that the existing CMM is not quite complete. In this case, the root stage element is marked as inserted. That is, the root stage element is inserted into the existing CMM as a root stage element of the existing CMM. As to the child stage elements of the root stage element in the new CMM which is marked as compounded, if the child stage element is marked as inserted, it is inserted into the existing CMM as a child stage element of the root stage element. Likewise, as to the child task elements of a child stage element in the new CMM which is marked as compounded, if the child task element is marked as inserted, it is inserted into the existing CMM as a child task element of the child stage element. As to the child data elements of the root stage element in the new CMM which is marked as compounded, if the child data element is marked as inserted, it is inserted into the existing CMM as a child data element of the root stage element.

In another embodiment, if it is judged in step 704 or 708 that the minimum match cost is smaller than the first threshold, it is further judged whether several similar minimum match costs have been obtained. For example, this is implemented by judging whether the difference between the minimum match cost and its larger neighbors is larger than a second threshold. If the difference is judged to be larger than the second threshold, this indicates that several similar minimum match costs have not been obtained. Thus, the to-be-aligned element is marked as compounded in step 712. If the difference is judged to be smaller than or equal to the second threshold, this indicates that several similar minimum match costs have been obtained. In this case, further judgment is made by using constraints. Likewise, if it is judged in step 708 that the minimum match cost is larger than or equal to the first threshold, further judgment is made by using constraints.

For example, when make judgment by using constraints, the matching element is determined according to the similarity between the constraints for the to-be-aligned element and the constraints for the to-be-matched elements. The criteria for judging the similarity includes: both the to-be-aligned element and the matching element have no constraints (e.g., if the to-be-aligned element has no constraints, the element in the to-be-matched elements which has no constraints are determined as the matching element); the constraint for the to-be-aligned element and the constraint for the matching elements are similar to each other in property (e.g., if the to-be-aligned element has temporal constraint, the element in the to-be-matched elements which has temporal constraint is determined as the matching element); the constraint between two child elements of the to-be-aligned element and the constraint between two child elements of the matching elements are similar to each other in property (e.g., if there exists temporal constraint between two child elements of the to-be-aligned element, the element in the to-be-matched elements which has temporal constraint between its two child elements are determined as the matching element); and so on. In this way, if the matching element has been found according to constraints, the to-be-aligned element is marked as compounded with the matching element. Otherwise, the to-be-aligned element is marked as inserted.

It should be noted that although the match costs between names of child elements of the to-be-aligned element and names of child elements of the to-be-matched elements are brought into the calculation of the minimum match cost when it is judged in step 704 that the minimum match cost is larger than or equal to the first threshold, the steps 702 and 704 are omitted and the step 706 is directly performed in another embodiment.

FIG. 8(a) shows an examples of CMM in healthcare scenario. In this figure, CHF Ambulatory Care Phase III represents chronic heart failure Ambulatory Care Phase III, sc is the abbreviation of Serum Creatinine, ACEI represents angiotensin converting enzyme inhibitor. The CMM shown in FIG. 8(a) is expressed as follows:

```
<stage id="1" name="CHF Ambulatory Care Phase III">
  <data id="2" name="sc" value="">
  <stage id="3" name="Baseline">
    <task id="4" name="Serum Creatinine" output="sc" />
    <task id="5" name="ACEI" constraints="N4 is started; D2<=2.5" />
  <stage id="6" name="Follow-up" constraints="N5 is started">
    <task id="7" name="Blood Pressure" />
<task id="8" name="Serum Potassium" />
```

Figure 8:
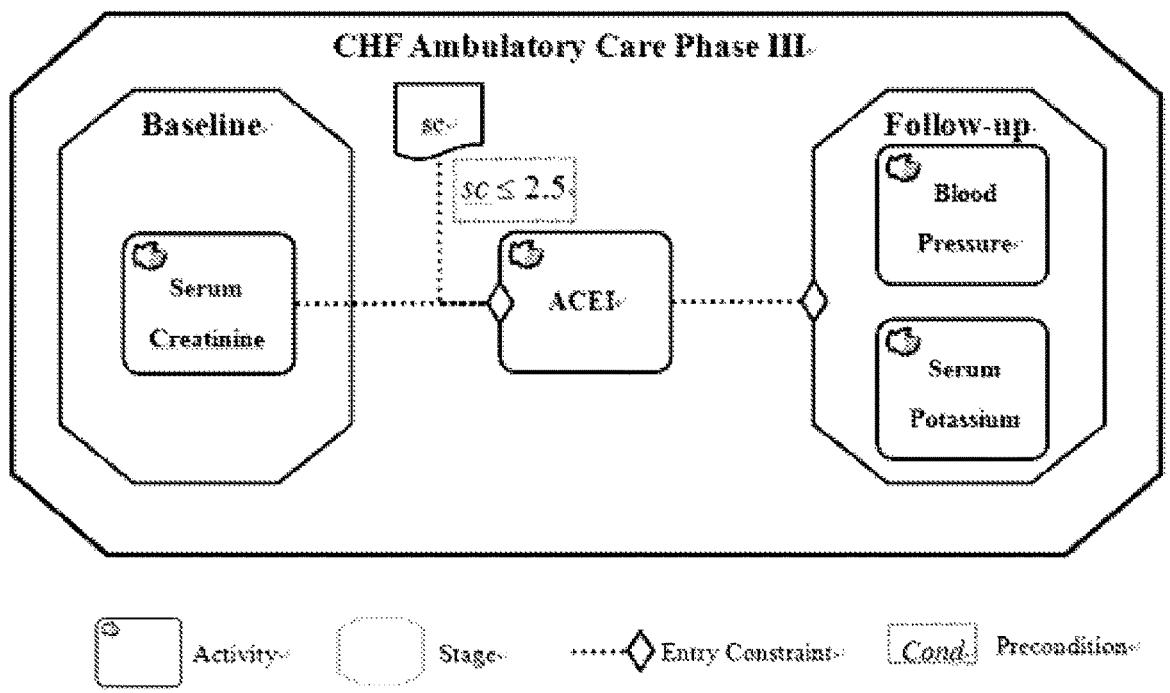
FIGS. 8(a) and 8(b) show examples of CMMs in healthcare scenarios.
Figure 8:
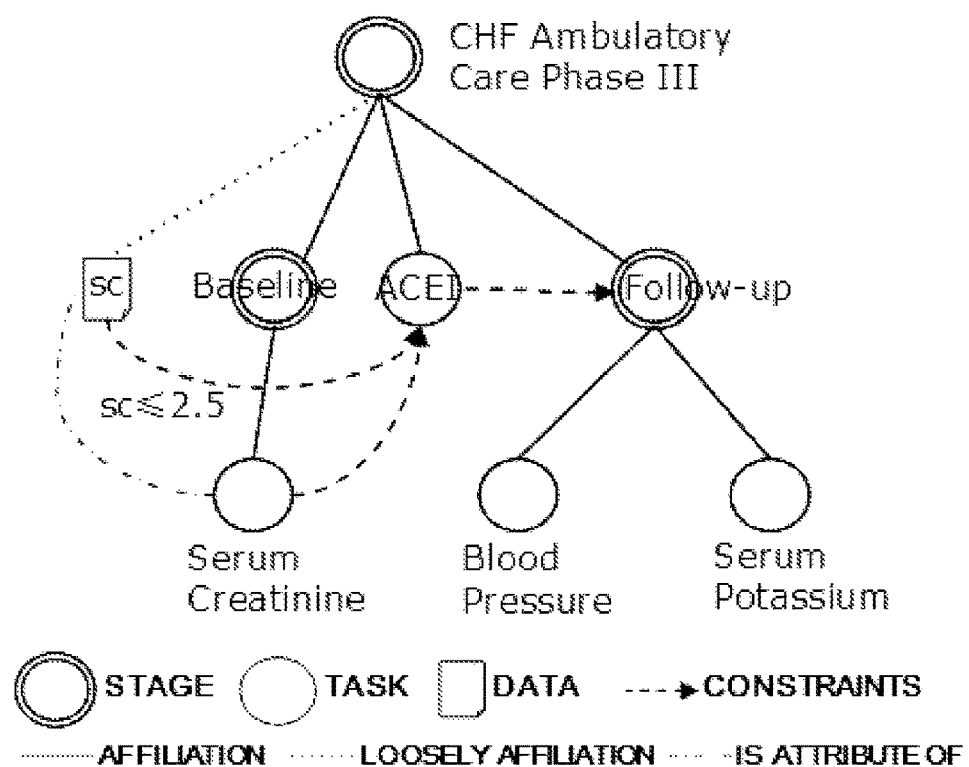
Figure 9:
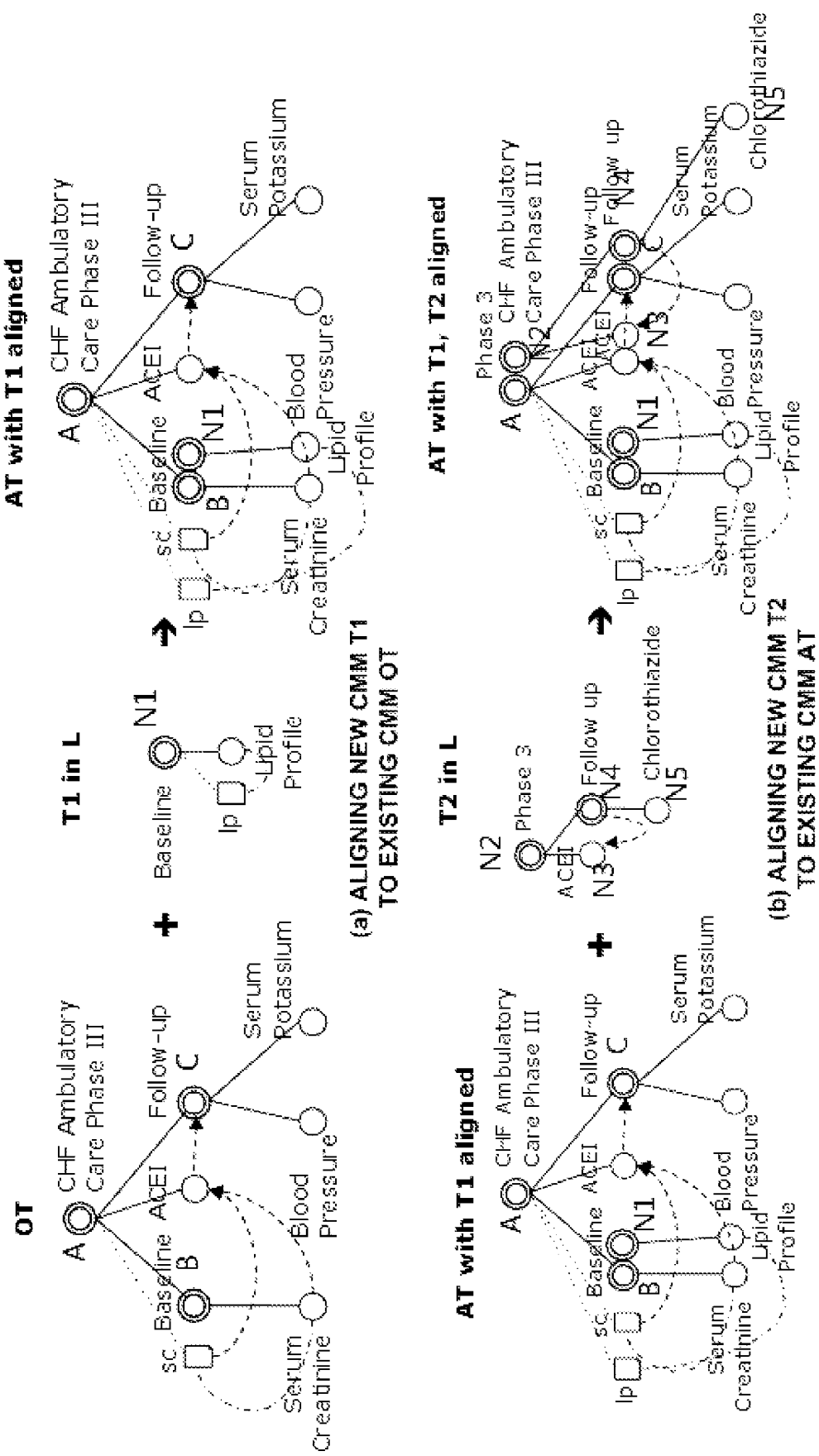
FIGS. 9(a) and 9(b) show examples of an aligning process according to an embodiment of the present disclosure.

FIG. 8(b) shows a tree diagram corresponding to the CMM of FIG. 8(a). The existing CMM shown in FIG. 8 is provided by the CMM modeling unit 210, and is also received through a communication network from a user who needs CMM fusing service.

FIGS. 9(a) and 9(b) show examples of an aligning process according to an embodiment of the present disclosure. As shown in FIG. 9(a), the existing CMM OT (Original Model Tree) is the existing CMM shown in FIG. 8(b), T1 is the first new CMM piece in a set of new CMM pieces L obtained by transformation. In order to align the new CMM piece T1 to the existing CMM OT, according to the flow chart shown in FIGS. 6 and 7, the minimum match cost between the name of the root stage node N1 of T1 and the names of respective stage nodes A, B and C of OT are calculated at first. The calculated result is as follows:

$M_1(N1,A)$=Dist("Baseline","CHF Ambulatory Care Phase III")/[StringLength("Baseline"+"CHF . . . ")]=29/37=0.78

$M_1(N1,B)$=Dist("Baseline",Baseline")/[StringLength("Baseline"+"Baseline")]=0/16=0

$M_1(N1,C)$=Dist("Baseline","Follow-up")/[StringLength("Baseline"+"Follow-up")]=17/17=1

$M_{min1}(N1,Y)$=Min($M1(N1,A),M1(N1,B),M1(N1,C)$)=Min(0.78,0,1)=0,Y=B,

Because $M_{min1}(N1,B)$<0.5,Align(N1)=(B,"compound")

As shown above, because the minimum match cost is 0 which is smaller than the threshold 0.5, the root stage node N1 is marked as compounded with the stage node B of OT. Likewise, the similar aligning process is applied to the child task node Lipid Profile and child data node lp (the abbreviation of Lipid Profile) of N1, thereby marking both as inserted. It should be noted that the above 0.5 is just an exemplary example of the threshold, and it may be adjusted by one skilled in the art according to various factors such as the specific application scenario for the CMM.

As shown in FIG. 9(b), the existing CMM has become the CMM AT which has been aligned with T1, and T2 represents the second new CMM piece in L. In order to align T2 to AT, according to the flow chart shown in FIGS. 6 and 7, the minimum match cost between the name of the root stage node N2 of T2 and the names of respective stage nodes A, B–N1 and C of AT are calculated at first. The calculated result is as follows:

$M_{min1}(N2,Y)$=Min($M_1(N2,A),M1(N2,B-N1),M_1(N2,C)$)=Min(0.64,Min(1,1),0.88)=0.64

Because $M_{min1}(N2,Y)$>=0.5,go on to calculate $M_{min2}(N2,Y)$

As shown above, because the calculated minimum match cost is 0.64 which is larger than 0.5, the minimum match cost between child elements of the root stage node N2 and child elements of respective stage nodes A, B–N1 and C of AT are calculated. The calculated result is as follows:

$N2_{chd}$={"Phase 3","ACEI","Follow up", "Chlorothiazide"}, $A_{chd}$={"CHF Ambulatory Case Phase III","sc", "Baseline","Baseline","ACEI", "Follow-up", . . . }, $M_{min2}(N2)$=Min( . . . ,$\Sigma_{x\ in\ Xchd} M_{min1}(X,A)$/number of $x$ in $X_{chd}$, . . . )=Min( . . . ,(0.64+0+0.06+1)/4 . . . )=0.43, Because $M_{min2}(N2,A)$<0.5,Align(N2)=(A,"compound")

As shown above, because the minimum match cost is 0.43 which is smaller than the threshold 0.5, the root stage node N2 is marked as compounded with the stage node A of AT. Likewise, the similar aligning process is applied to the child stage node N4-Follow up and the child task nodes N3-ACEI and N5-Chlorothiazide of N2, thereby marking N4 as compounded with the stage node C of AT, marking the task node N3 as compounded with the task node ACEI of AT, and marking the task node N5 as inserted.

It should be noted that although the aligning process between the new CMM and the existing CMM is described in FIGS. 9(a) and 9(b) by using new CMM pieces as an example, it is only an exemplary example provided for the purpose of explaining the principle of the embodiment of the present disclosure. It is apparent for one skilled in the art that the aligning method shown in FIGS. 6 and 7 can of course be applied to the case where a relatively larger new CMM is aligned to the existing CMM (the respective elements in the relatively larger new CMM are subjected to the aligning process respectively, or alternatively, the relatively larger new CMM is divided into a plurality of new CMM pieces and these new CMM pieces are subjected to the aligning process respectively).

Now the compounding process according to an embodiment of the present disclosure will be described with reference to FIG. 10. Firstly, in step 1002, a list of names of elements marked as compounded and their matching element is obtained. Because it is possible to align a plurality of new CMMs to an existing CMM at a time, there exists in the plurality of new CMMs one or more elements which are marked as compounded with one matching element. Then, the compounded name of the matching element in the existing CMM is determined according to the list of names. As an exemplary example, it is judged in step 1004 whether the name of the matching element contains meaningful keywords. For example, this is implemented by judging whether the name of the matching element contains only stop words in natural language processing technique. Generally, stop words refer to some most common, short function words, including words which are used to indicate grammatical relationship and has little meaning (e.g., preposition, conjunction, article, etc.). As an exemplary example, in addition to the function words, the stop words used in step 1004 further include reserved words for CMM (e.g., stage, task, etc.), and simple combination formed by letters and/or numbers which has no meaning. For example, if the name of a task element is "the task A", it is judged that the name has no meaningful keywords.

If it is judged in step 1004 that the name of the matching element contains meaningful keywords, the name of the matching element is used as the compounded name in step 1008 (i.e., the name of the matching element in the existing CMM is kept unchanged). On the other hand, if it is judged in step 1004 that the name of the matching element contains no meaningful keywords, the name of the matching element in the existing CMM is changed to the most occurred meaningful keyword in the list of names.

Then, in step 1010, a list of constraints for elements marked as compounded and their matching element is obtained. Likewise, because it is possible to align a plurality of new CMMs to an existing CMM at a time, there exists in the plurality of new CMMs one or more elements which are marked as compounded with one matching element. Then, in step 1012, it is judged whether the list contains contradictory constraints to each other. If it is judged in step 1012 that the list contains no contradictory constraints to each other, the process proceeds directly to step 1020.

On the other hand, if it is judged in step 1012 that the list contains contradictory constraints to each other, it is judged in step 1014 whether the support degrees for each one of the contradictory constraints are equal to each other. For example, the support degrees for each one of the contradictory constraints are calculated by calculating for each one of the contradictory constraints the number of occurrences in the list of constraints. If it is judged in step 1014 that the support degrees for each one of the contradictory constraints are equal to each other, the contradictory constraints are discarded in step 1018. On the other hand, if it is judged in step 1014 that the support degrees for each one of the contradictory constraints are not equal to each other, the constraint having lower support degree is discarded in step 1016. Finally, in step 1020, the elements in the new CMM which are marked as compounded are incorporated into the matching element of the existing CMM. For example, as to the attributes of a stage element, the following incorporating process is conducted: as to id, it is possible to only reserve the id of the matching element of the existing CMM; as to description, entry criteria and exit criteria, such attributes of the aligned elements of the new CMM are added into the corresponding attributes of the matching element of the existing CMM, or alternatively, it is possible to further judge whether there exists duplicate content thereby deleting the duplicate content. Likewise, as to the attributes of a task element and a data element, the similar incorporating process is conducted.

Now the inserting process according to an embodiment of the present disclosure will be described with reference to FIG. 11. Firstly, in step 1102, the elements in the new CMM which are marked as inserted are inserted into the existing CMM. As to the hierarchical location of the element marked as inserted, when the element is a root stage element, the element is inserted into the existing CMM as a root stage element; and when the element is not a root stage element, the element is inserted into the existing CMM as a child element of its parent element. That is, the hierarchical location of the element in the new CMM remains unchanged after it is inserted into the existing CMM. For example, as to a root stage element marked as inserted, it is inserted into the existing CMM as a root stage element. As to a child stage element which is marked as inserted and whose root stage element is marked as compounded, it is inserted into the existing CMM as a child stage element of the root stage element. The same holds true for the child task element and child data element. As to the content of the elements in the new CMM which are marked as inserted, as a simplest example, the element is inserted into the existing CMM with the content of the element remaining unchanged, such that the user can make modifications as needed at a later time when viewing the fused CMM through the CMM editing/viewing unit 214. However, when the element is inserted into the existing CMM, the content of the element is modified according to the specific situation (e.g., the requirement of the user).

Then, in step 1104, it is judged whether an attribute (e.g., output, entry/exit criteria) of the inserted stage or task element references an element which is marked as compounded. If it is judged in step 1104 that any attribute of the inserted stage or task element does not reference an element which is marked as compounded, the process proceeds directly to step 1108. On the other hand, if it is judged in step 1104 that any attribute of the inserted stage or task element references an element which is marked as compounded, the attribute is changed to reference the compounded element in step 1106.

Then, in step 1108, it is judged whether a constraint for the inserted stage or task element references an element which is marked as compounded. If it is judged in step 1108 that any constraint for the inserted stage or task element does not reference an element which is marked as compounded, the inserting process ends. On the other hand, if it is judged in step 1108 that any constraint of the inserted stage or task element references an element which is marked as compounded, the constraint is changed to reference the compounded element. Then, the inserting process ends.

Figure 12:
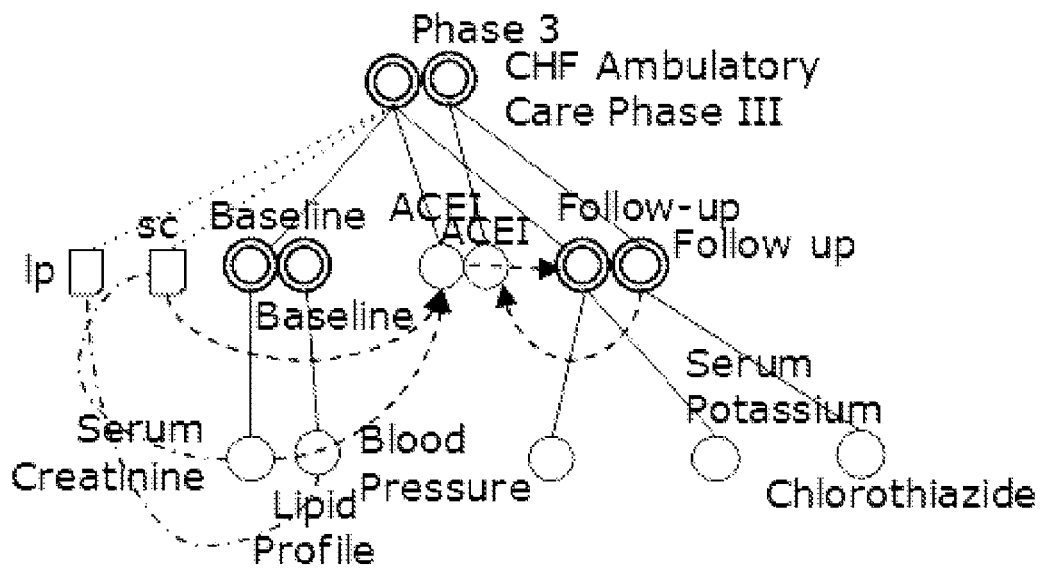
FIGS. 12(a) and 12(b) show examples of a fusing process according to an embodiment of the present disclosure.
Figure 12:
Figure 12:
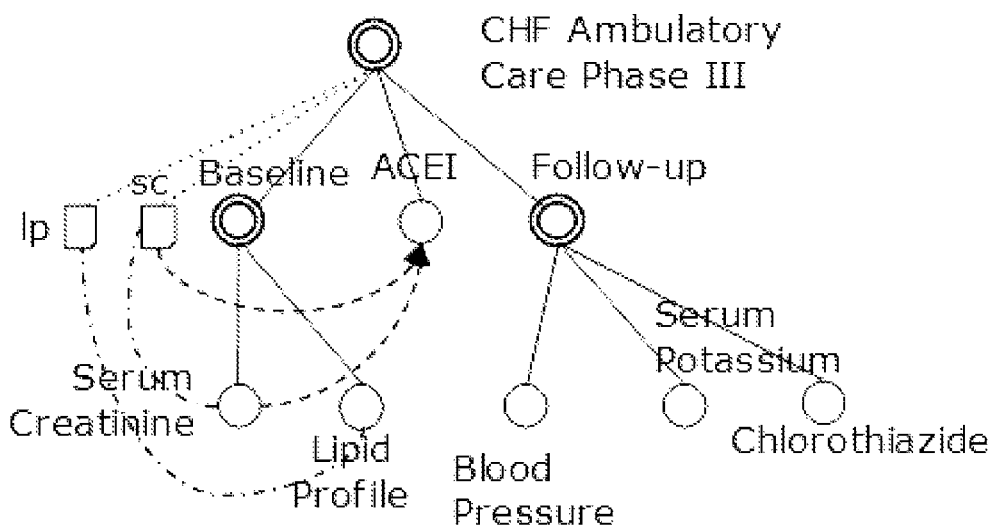

FIG. 12 shows examples of a fusing process according to an embodiment of the present disclosure. As shown, the stage node CHF Ambulatory Care Phase III of the existing CMM is compounded with the stage node Phase 3 of the new CMM piece. Because the original name CHF Ambulatory Care Phase III contains meaningful keywords, it remains unchanged after the compounding process. The stage node Baseline of the existing CMM is compounded with the stage node Baseline of the new CMM piece, the stage node Follow-up of the existing CMM is compounded with the stage node Follow up of the new CMM piece, and the task node ACEI of the existing CMM is compounded with the task node ACEI of the new CMM piece, and the names of the above nodes of the existing CMM remain unchanged. Meanwhile, the task nodes Lipid Profile and Chlorothiazide of the new CMM piece are inserted into the existing CMM as they are.

Likewise, it should be noted that although the fusing process between the new CMM and the existing CMM is described in FIG. 12 by using new CMM pieces as an example, it is only an exemplary example provided for the purpose of explaining the principle of the embodiment of the present disclosure. It is apparent for one skilled in the art that the fusing method shown in FIGS. 10 and 11 can of course be applied to the case where a relatively larger new CMM is aligned to the existing CMM.

It can be known from the above description that various embodiments of the present disclosure can provide the following advantages: (1) automatically improving knowledge in a CMM, and offering intelligent assistance and guidance to knowledge workers; (2) dissolving knowledge isolated islands by fusing knowledge from diverse sources; (3) making knowledge in a CMM be up-to-date, complete and practical; and (4) saving greatly time and labor for knowledge workers.

Figure 13:
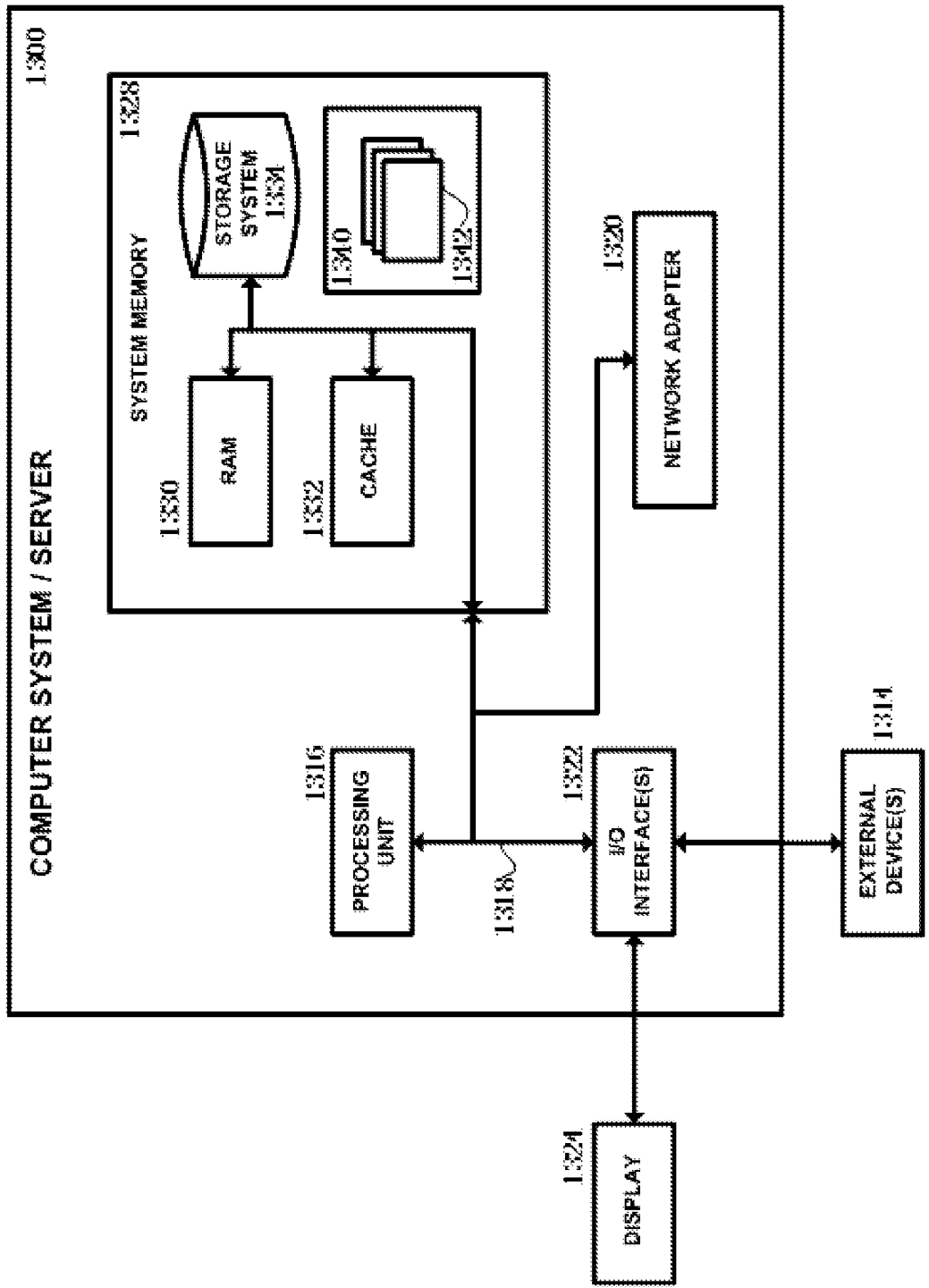
FIG. 13 shows a block diagram of an exemplary computer system/server which is applicable to implement the embodiments of the present disclosure.

Referring now to FIG. 13, in which an exemplary computer system/server 1300 which is applicable to implement the embodiments of the present disclosure is shown. Computer system/server 1300 is only illustrative and is not intended to suggest any limitation as to the scope of use or functionality of embodiments of the invention described herein.

As shown in FIG. 13, computer system/server 1300 is shown in the form of a general-purpose computing device. The components of computer system/server 1300 may include, but are not limited to, one or more processors or processing units 1316, a system memory 1328, and a bus 1318 that couples various system components including system memory 1328 to processor 1316.

Bus 1318 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 1300 typically includes a variety of computer system readable media. Such media may be any available media that is accessible by computer system/server 1300, and it includes both volatile and non-volatile media, removable and non-removable media.

System memory 1328 can include computer system readable media in the form of volatile memory, such as random access memory (RAM) 1330 and/or cache memory 1332. Computer system/server 1300 may further include other removable/non-removable, volatile/non-volatile computer system storage media. By way of example only, storage system 1334 can be provided for reading from and writing to a non-removable, non-volatile magnetic media (not shown in FIG. 13 and typically called a "hard drive"). Although not shown in FIG. 13, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1318 by one or more data media interfaces. As will be further depicted and described below, memory 1328 may include at least one program product having a set (e.g., at least one) of program modules that are configured to carry out the functions of embodiments of the invention.

Program/utility 1340, having a set (at least one) of program modules 1342, may be stored in memory 1328 by way of example, and not limitation, as well as an operating system, one or more application programs, other program modules, and program data. Each of the operating system, one or more application programs, other program modules, and program data or some combination thereof, may include an implementation of a networking environment. Program modules 1342 generally carry out the functions and/or methodologies of embodiments of the invention as described herein.

Computer system/server 1300 may also communicate with one or more external devices 1314 such as a keyboard, a pointing device, a display 1324, etc.; one or more devices that enable a user to interact with computer system/server 1300; and/or any devices (e.g., network card, modem, etc.) that enable computer system/server 1300 to communicate with one or more other computing devices. Such communication can occur via Input/Output (I/O) interfaces 1322. Still yet, computer system/server 1300 can communicate with one or more networks such as a local area network (LAN), a general wide area network (WAN), and/or a public network (e.g., the Internet) via network adapter 1320. As depicted, network adapter 1320 communicates with the other components of computer system/server 1300 via bus 1318. It should be understood that although not shown, other hardware and/or software components could be used in conjunction with computer system/server 1300. Examples, include, but are not limited to: microcode, device drivers, redundant processing units, external disk drive arrays, RAID systems, tape drives, and data archival storage systems, etc.

It should be noted that as to the above mentioned embodiments in which the CMM aligning unit 206 and the CMM fusing unit 208 are combined as one apparatus, or the CMM aligning unit 206 and the CMM fusing unit 208 are combined with the CMM transforming unit 202 to become one apparatus, such apparatus does not include the display 1324, the network adapter 1320 and the external devices 1314.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer implemented method for processing a case management model (CMM), the method comprising:
    obtaining, by a computer system, an existing CMM having a plurality of elements, wherein the plurality of elements are transformed from a data intermediate format (DIF) table and clustered by time using a data miner or from a text intermediate format (TIF) table of unstructured data using a text mining;
    obtaining, by the computer system, a new CMM having at least one element, wherein the at least one element is transformed from the DIF table and clustered by time using the data miner or from the TIF table of unstructured data using the text mining;
    aligning, by the computer system, an element from the at least one element associated with the new CMM to an element from the plurality of elements associated with the existing CMM according to match costs between the at least one element of the new CMM and the plurality of elements of the existing CMM,
        wherein the match costs are calculated by utilizing edit distance,
        wherein the aligned elements include at least one matching element associated with at least one keyword in the existing CMM,
        wherein the at least one keyword is utilized as the name of the matching element associated with the existing CMM,
    wherein determining a lack of at least one keyword, the name of the matching element including a most occurred keyword based on a list of names associated with the existing CMM;

fusing, via a fusing unit of the computer system, the element of the new CMM into the existing CMM based on a first threshold associated with the match cost between the aligned elements,
  wherein the first threshold is provided and adjusted by a user based on a plurality of factors; and
automatically modifying, by the computer system, the existing CMM based on the fused element of the new CMM.

2. The method according to claim 1, wherein aligning the element of the new CMM to the element of the existing CMM comprises:
  aligning the element of the new CMM to the element of the existing CMM which has a minimum match cost with the element of the new CMM.

3. The method according to claim 1, wherein fusing the element of the new CMM into the existing CMM comprises:
  compounding the element of the new CMM belonging to the aligned elements into the element of the existing CMM belonging to the aligned elements, when the match cost between the aligned elements is less than the first threshold.

4. The method according to claim 3, wherein compounding the element of the new CMM into the element of the existing CMM comprises:
  determining a compounded name of an aligned element of the existing CMM according to the list of names of the aligned elements.

5. The method according to claim 3, wherein compounding the element of the new CMM into the element of the existing CMM comprises:
  when the aligned elements have contradictory constraints to each other, determining for each one of the contradictory constraints, a support degree in a list of constraints of the aligned elements;
  when the support degrees for each one of the contradictory constraints are equal to each other, discarding both of the contradictory constraints; and
  when the support degrees for each one of the contradictory constraints are not equal to each other, keeping the contradictory constraint having higher support degree.

6. The method according to claim 1, wherein fusing the element of the new CMM into the existing CMM comprises:
  inserting the element of the new CMM into the existing CMM, when the match cost between the aligned elements is larger than or equal to the first threshold.

7. The method according to claim 6, wherein inserting the element of the new CMM into the existing CMM comprises:
  when an attribute or a constraint of the inserted element references an element which is compounded into the existing CMM, changing the attribute or the constraint to reference the compounded element.

8. The method according to claim 1, wherein the match costs between the at least one element of the new CMM and the plurality of elements of the existing CMM comprise:
  match costs between children elements of the at least one element of the new CMM and children elements of the plurality of elements of the existing CMM.

9. The method according to claim 1, wherein the element of the new CMM is fused into the existing CMM based on at least one knowledge source comprising structured knowledge source and/or unstructured knowledge source.

10. The method according to claim 1, wherein obtaining the existing CMM comprises:
  receiving the existing CMM from a user through a communication network;
  wherein obtaining the new CMM comprises:
  receiving from the user through the communication network an analytics result obtained by analyzing at least one knowledge source, the at least one knowledge source comprising structured knowledge source and/or unstructured knowledge source; and
  transforming the analytics result to the new CMM;
  wherein the method further comprises:
  transmitting the fused CMM to the user through the communication network.

11. A computer system for processing a case management model (CMM), comprising:
  receiving, by an aligning unit, an existing CMM having a plurality of elements, wherein the plurality of elements are transformed from a data intermediate format (DIF) table and clustered by time using a data miner or from a text intermediate format (TIF) table of unstructured data using a text mining and a new CMM having at least one element, wherein the at least one element is transformed from the DIF table and clustered by time using the data miner or from the TIF table of unstructured data using the text mining;
  aligning an element from the at least one element associated with the new CMM to an element from the plurality of elements associated with the existing CMM according to match costs between the at least one element of the new CMM and the plurality of elements of the existing CMM,
    wherein the match costs are calculated by utilizing edit distance,
    wherein the aligned elements include at least one matching element associated with at least one keyword in the existing CMM,
    wherein the at least one keyword is utilized as the name of the matching element associated with the existing CMM,
  wherein determining a lack of at least one keyword, the name of the matching element including a most occurred keyword based on a list of names associated with the existing CMM;
  fusing, by a fusing unit, the element of the new CMM into the existing CMM based on a first threshold associated with the match cost between the aligned elements,
    wherein the first threshold is provided and adjusted by a user based on a plurality of factors; and
  automatically modifying the existing CMM based on the fused element of the new CMM.

12. The computer system according to claim 11, wherein the aligning unit is configured to:
  align the element of the new CMM to the element of the existing CMM which has a minimum match cost with the element of the new CMM.

13. The computer system according to claim 11, wherein the fusing unit is configured to:
  compound the element of the new CMM belonging to the aligned elements into the element of the existing CMM belonging to the aligned elements, when the match cost between the aligned elements is less than the first threshold.

14. The computer system according to claim 13, wherein the fusing unit is configured to:
  determine a compounded name of an aligned element of the existing CMM according to the list of names of the aligned elements.

15. The computer system according to claim 13, wherein the fusing unit is configured to:
  when the aligned elements have contradictory constraints to each other, determine for each one of the contradictory constraints, a support degree in a list of constraints of the aligned elements;
  when the support degrees for each one of the contradictory constraints are equal to each other, discard both of the contradictory constraints; and
  when the support degrees for each one of the contradictory constraints are not equal to each other, keep the contradictory constraint having higher support degree.

16. The computer system according to claim 11, wherein the fusing unit is configured to:
  insert the element of the new CMM into the existing CMM, when the match cost between the aligned elements is larger than or equal to the first threshold.

17. The computer system according to claim 11, wherein the match costs between the at least one element of the new CMM and the plurality of elements of the existing CMM comprise:
  match costs between children elements of the at least one element of the new CMM and children elements of the plurality of elements of the existing CMM.

18. The computer system according to claim 11, further comprising:
  receiving unit configured to receive from a user through a communication network the existing CMM and an analytics result obtained by analyzing at least one knowledge source, the at least one knowledge source comprising structured knowledge source and/or unstructured knowledge source;
  transforming unit configured to transform the analytics result to the new CMM; and
  transmitting unit configured to transmit the fused CMM to the user through the communication network.

19. The computer system according to claim 11, further comprising:
  transforming unit configured to receive an analytics result obtained by analyzing at least one knowledge source, and transform the analytics result to the new CMM, the at least one knowledge source comprising structured knowledge source and/or unstructured knowledge source;
  modeling unit configured to enable a user to build a CMM;
  storing unit configured to store a CMM; and
  editing unit configured to enable the user to edit and/or view a CMM.

20. A computer program product for processing a case management model (CMM), comprising:
  one or more computer-readable storage medium and program instructions stored on at least one of the one or more tangible storage medium, the program instructions executable by a processor, the program instructions comprising:
  program instructions to obtain an existing CMM having a plurality of elements, wherein the plurality of elements are transformed from a data intermediate format (DIF) table and clustered by time using a data miner or from a text intermediate format (TIF) table of unstructured data using a text mining;
  program instructions to obtain a new CMM having at least one element, wherein the at least one element is transformed from the DIF table and clustered by time using the data miner or from the TIF table of unstructured data using the text mining;
  program instructions to align an element from the at least one element associated with the new CMM to an element from the plurality of elements associated with the existing CMM according to match costs between the at least one element of the new CMM and the plurality of elements of the existing CMM,
    wherein the match costs are calculated by utilizing edit distance,
    wherein the aligned elements include at least one matching element associated with at least one keyword in the existing CMM,
    wherein the at least one keyword is utilized as the name of the matching element associated with the existing CMM,
  wherein determining a lack of at least one keyword, the name of the matching element including a most occurred keyword based on a list of names associated with the existing CMM;
  program instructions to fuse, via a fusing unit, the element of the new CMM into the existing CMM based on a first threshold associated with the match cost between the aligned elements,
    wherein the first threshold is provided and adjusted by a user based on a plurality of factors; and
  program instructions to automatically modify the existing CMM based on the fused element of the new CMM.

* * * * *